US011589831B2

(12) United States Patent
Song et al.

(10) Patent No.: US 11,589,831 B2
(45) Date of Patent: Feb. 28, 2023

(54) X-RAY APPARATUS AND METHOD OF ACQUIRING MEDICAL IMAGE THEREOF

(71) Applicant: SAMSUNG ELECTRONICS CO., LTD., Suwon-si (KR)

(72) Inventors: Jeong Yong Song, Bucheon-si (KR); Byeong Won Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 0 days.

(21) Appl. No.: 17/218,723

(22) Filed: Mar. 31, 2021

(65) Prior Publication Data
US 2021/0212641 A1 Jul. 15, 2021

Related U.S. Application Data

(63) Continuation of application No. 15/822,710, filed on Nov. 27, 2017, now Pat. No. 11,083,421.
(Continued)

(30) Foreign Application Priority Data

Mar. 20, 2017 (KR) .................. 10-2017-0034381

(51) Int. Cl.
A61B 6/00 (2006.01)
G01T 5/00 (2006.01)
(Continued)

(52) U.S. Cl.
CPC .......... *A61B 6/4014* (2013.01); *A61B 6/4405* (2013.01); *A61B 6/5282* (2013.01);
(Continued)

(58) Field of Classification Search
CPC .......... A61B 6/03; A61B 6/04; A61B 6/4014; A61B 6/4405; A61B 6/462; A61B 6/465;
(Continued)

(56) References Cited

U.S. PATENT DOCUMENTS 5,270,925 A 12/1993 Stegehuis
6,233,365 B1 5/2001 Teruhiko
(Continued)

FOREIGN PATENT DOCUMENTS

CN 105574828 A 5/2016
CN 105682558 A 6/2016
(Continued)

OTHER PUBLICATIONS

Communication dated Aug. 4, 2021 by the Korean Intellectual Property Office in counterpart Korean Patent Application No. 10-2017-0034381.
(Continued)

Primary Examiner — Dani Fox
(74) Attorney, Agent, or Firm — Sughrue Mion, PLLC

(57) ABSTRACT

Disclosed herein is an X-ray apparatus for acquiring a medical image, and a method of using said X-ray apparatus, said method comprising the steps of: acquiring an original radiation image of a target object and capturing condition information of the object; acquiring a scatter radiation image related to the original radiation image by inputting the original radiation image and the capturing condition information to a learning network model configured to estimate scatter radiation; and acquiring a scatter radiation-processed medical image from the original radiation image on the basis of the original radiation image and the scatter radiation image, wherein the learning network model configured to estimate scatter radiation is a learning network model taught using a plurality of scatter radiation images and a plurality of pieces of capturing condition information related to each of the plurality of scatter radiation images.

16 Claims, 16 Drawing Sheets

Related U.S. Application Data

(60) Provisional application No. 62/426,344, filed on Nov. 25, 2016.

(51) Int. Cl.
  *G06T 5/00* (2006.01)
  *G06N 3/04* (2023.01)
  *A61B 6/03* (2006.01)
  *A61B 6/04* (2006.01)

(52) U.S. Cl.
  CPC ......... *A61B 6/5294* (2013.01); *G06N 3/0454* (2013.01); *G06T 5/002* (2013.01); *G06T 5/003* (2013.01); *A61B 6/03* (2013.01); *A61B 6/04* (2013.01); *A61B 6/462* (2013.01); *A61B 6/465* (2013.01); *A61B 6/5205* (2013.01); *A61B 6/544* (2013.01); *A61B 6/563* (2013.01); *A61B 6/584* (2013.01); *G06T 2207/20081* (2013.01)

(58) Field of Classification Search
  CPC ... A61B 6/5205; A61B 6/5282; A61B 6/5294; A61B 6/544; A61B 6/563; A61B 6/584; G06N 3/0454; G06T 5/002; G06T 5/003; G06T 2207/20081
  See application file for complete search history.

(56) References Cited

U.S. PATENT DOCUMENTS

| | | | |
|---|---|---|---|
| 10,342,504 | B2 | 7/2019 | Star-Lack et al. |
| 10,512,441 | B2 | 12/2019 | Kyriakou |
| 2008/0013673 | A1 | 1/2008 | Ruhmschopf |
| 2008/0075347 | A1 | 3/2008 | Ruhrnschopf |
| 2012/0148156 | A1 | 6/2012 | Sehnert |
| 2014/0226794 | A1 | 8/2014 | Am et al. |
| 2015/0201895 | A1 | 7/2015 | Suzuki |
| 2015/0251018 | A1 | 9/2015 | Tajima et al. |
| 2015/0342554 | A1 | 12/2015 | Mentrup et al. |
| 2016/0012592 | A1 | 1/2016 | Chou et al. |
| 2016/0086078 | A1 | 3/2016 | Ji et al. |
| 2016/0235385 | A1 | 8/2016 | Enomoto et al. |

FOREIGN PATENT DOCUMENTS

| | | |
|---|---|---|
| CN | 105682559 A | 6/2016 |
| CN | 107516330 A | 12/2017 |
| DE | 69402041 T2 | 10/1997 |
| JP | 2015-126864 A | 7/2015 |
| WO | 2016/168194 | 10/2016 |

OTHER PUBLICATIONS

Search Report dated Feb. 8, 2018, issued by the International Search Authority in International application No. PCT/KR2017/013510 (PCT/ISA/210).

Communication dated Apr. 25, 2018, issued by the European Patent Office in counterpart European application No. 17203326.8.

Cortes et al., "Support-Vector Networks", Sep. 1, 1995, Machine Learning, vol. 20, No. 3, XP000569418, 25 pages total.

Communication dated Mar. 20, 2019, issued by the European Patent Office in counterpart European Application No. 17203326.8.

Communication dated Nov. 21, 2022 issued by the China National Intellectual Property English Administration in counterpart Chinese Patent Application No. 201780073254.8.

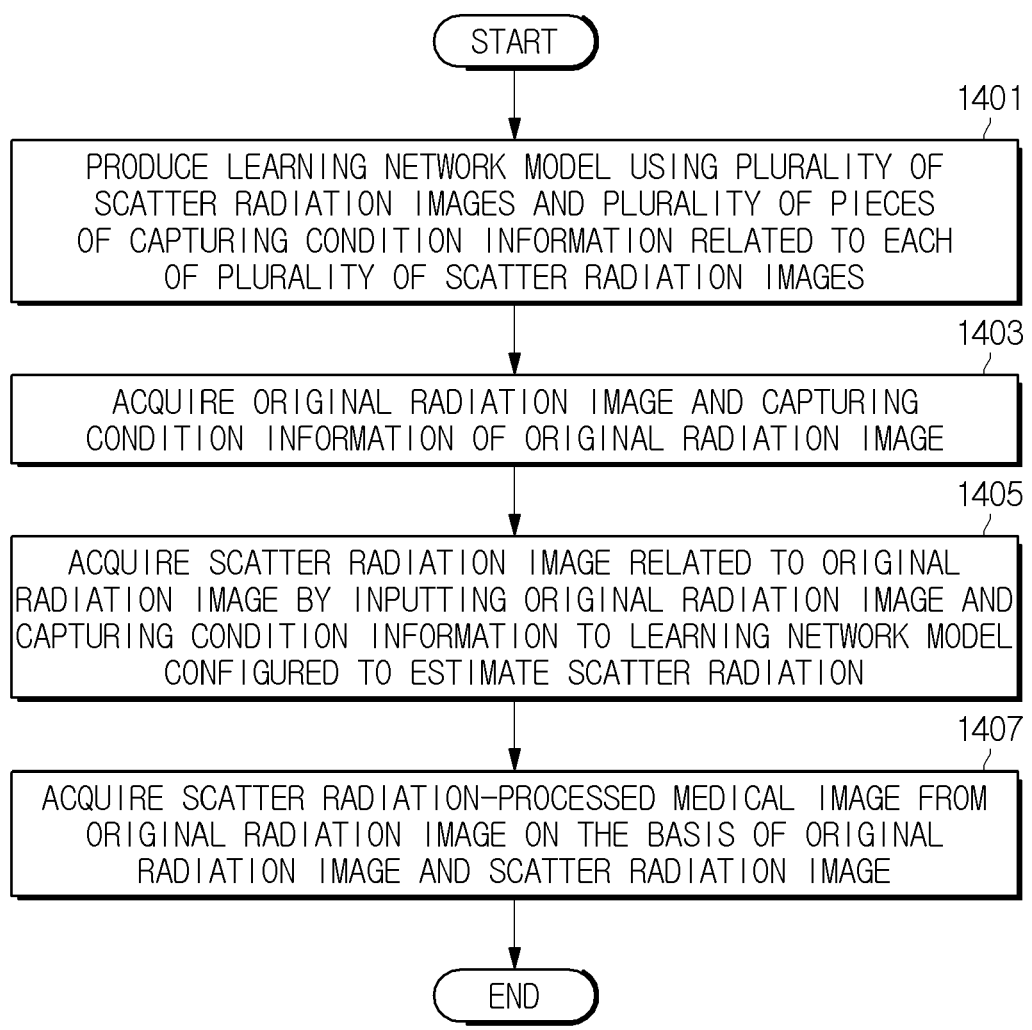

X-RAY APPARATUS AND METHOD OF ACQUIRING MEDICAL IMAGE THEREOF

CROSS-REFERENCE TO RELATED APPLICATION

This application is a continuation of U.S. patent application Ser. No. 15/822,710, filed on Nov. 27, 2017, in the U.S. Patent and Trademark Office, which claims the benefit of U.S. Provisional Application No. 62/426,344, filed on Nov. 25, 2016, in the U.S. Patent and Trademark Office, and Korean Patent Application No. 10-2017-0034381, filed on Mar. 20, 2017, in the Korean Intellectual Property Office, the disclosures of which are incorporated herein by reference in their entireties.

BACKGROUND

1. Field

Exemplary embodiments of the present disclosure relate to an X-ray apparatus and a method of acquiring a medical image thereof, and more particularly, to a method of acquiring a medical image having improved quality by processing a radiation image of an object detected by an X-ray apparatus, and an X-ray apparatus for performing the method.

2. Description of the Related Art

X-ray apparatuses are able to irradiate an object with X-rays to acquire a radiation image thereof. In this case, radiation detected by an X-ray detector may include scatter radiation that degrades image quality in addition to primary radiation including important information.

To filter scatter radiation, an anti-scatter physical grid may be used between an object and an X-ray detector.

When an anti-scatter physical grid is used, accurate alignment between the X-ray detector and a tube of an X-ray emitter is required. However, it is difficult to align the X-ray detector with respect to the tube of an X-ray emitter, and thus a user may avoid using the anti-scatter physical grid.

In addition, the use of the anti-scatter physical grid may be avoided due to the difficulty in attaching and detaching the anti-scatter physical grid to and from the X-ray detector and the difficulty in disinfection management thereof.

When the anti-scatter physical grid is not used, quality of an X-ray image may be significantly reduced and, accordingly, there is a need to compensate for the quality of the X-ray image with an algorithm.

For example, to remove a scatter radiation image from an original radiation image detected by an X-ray detector, a kernel database consisting of a plurality of scatter kernels may be used in consideration of characteristics according to a region or thickness of a body site, e.g., a part of body or a location on or in the body. In this case, when the original radiation image is input, an X-ray apparatus may apply different scatter kernels according to the region or thickness of the body site to acquire a radiation image from which scatter radiation is removed.

SUMMARY

To remove scatter radiation by applying a plurality of scatter kernels in an X-ray apparatus, it is beneficial to accurately estimate characteristics based on a body site.

For example, when scatter kernels are applied according to a region of a body site, it is necessary for an X-ray apparatus to accurately measure characteristics according to the region of the body site and connection parts between body sites. In addition, when different scatter kernels are applied according to a thickness of the body site, it is necessary for the X-ray apparatus to accurately measure the thickness of the body site.

In addition, the human body allows combinations and changes of numerous substances in consideration of a body type and health conditions of a patient, and thus, when a kernel database consisting of a limited number of a plurality of scatter kernels is used, there may be a limitation in improving quality of a radiation image.

Accordingly, a recent novel technology may be considered. For example, an imaging technology using an artificial intelligence (AI) system instead of using simple search for database has recently emerged. The AI system is a computer system implementing human-level intelligence, in which a machine itself learns and judges, and thus a recognition rate increases as the computer system is used. An AI technology consists of element technologies that mimic functions such as recognition, judgement, and the like of the human brain using a learning network model that uses an algorithm to classify/learn characteristics of input data.

The element technologies may include, for example, at least one of linguistic comprehension techniques for recognizing human languages/characters, visual comprehension techniques for recognizing objects as human vision, inference/prediction techniques for determining and logically inferring and predicting information, knowledge expression techniques for processing human experience information as knowledge data, and operation control techniques for controlling autonomous driving of vehicles and robotic motion. Among these, visual comprehension is a technique for recognizing and processing an object as human vision, and includes object recognition, object tracking, image searching, human recognizing, scene understanding, spatial understanding, image enhancing, and the like.

Therefore, it is an aspect of the present disclosure is to improve quality of a radiation image of an object detected by an X-ray apparatus, by using such an AI technology.

Additional aspects of the disclosure will be set forth in part in the description which follows and, in part, will be obvious from the description, or may be learned by practice of the disclosure.

In accordance with one aspect of the present disclosure, a method of acquiring a medical image of an X-ray apparatus includes acquiring an original radiation image of a target object and capturing condition information of the target object; acquiring a scatter radiation image related to the original radiation image by inputting the original radiation image and the capturing condition information to a learning network model configured to estimate scatter radiation; and acquiring a scatter radiation-processed medical image from the original radiation image on the basis of the original radiation image and the scatter radiation image, wherein the learning network model configured to estimate scatter radiation is a learning network model taught using a plurality of scatter radiation images and a plurality of pieces of capturing condition information related to each of the plurality of scatter radiation images.

In accordance with another aspect of the present disclosure, a method of acquiring a medical image of an X-ray apparatus includes acquiring an original radiation image of a target object and capturing condition information of the target object; and acquiring a scatter radiation-processed medical image from the original radiation image by inputting the original radiation image and the capturing condition information to a learning network model configured to estimate a scatter radiation-processed medical image, wherein the learning network model configured to estimate a scatter radiation-processed medical image is a learning network model taught using a plurality of original radiation images and a plurality of pieces of capturing condition information related to each of the plurality of original radiation images.

In accordance with another aspect of the present disclosure, an X-ray apparatus includes an X-ray emitter configured to emit X-rays to photograph a target object; an X-ray detector configured to detect X-rays emitted from the X-ray emitter passed through the object; a controller electrically connected to the X-ray emitter and the X-ray detector to control the X-ray apparatus; and a memory electrically connected to the controller, wherein the memory is configured to store instructions allowing the controller to perform a control operation to acquire a scatter radiation image related to an original radiation image of the object acquired from the X-ray detector by inputting the original radiation image and capturing condition information of the object to a learning network model configured to estimate scatter radiation, and to acquire a scatter radiation-processed medical image from the original radiation image on the basis of the original radiation image and the scatter radiation image, when the X-ray apparatus operates, wherein the learning network model configured to estimate scatter radiation is a learning network model taught using a plurality of scatter radiation images and a plurality of pieces of capturing condition information related to each of the plurality of scatter radiation images.

In accordance with another aspect of the present disclosure, an X-ray apparatus includes an X-ray emitter configured to emit X-rays to photograph an object; an X-ray detector configured to detect X-rays emitted from the X-ray emitter and passed through the object; a controller electrically connected to the X-ray emitter and the X-ray detector to control the X-ray apparatus; and a memory electrically connected to the controller, wherein the memory is configured to store instructions allowing the controller to perform a control operation to acquire a scatter radiation-processed medical image from an original radiation image of the object acquired from the X-ray detector by inputting the original radiation image and capturing condition information of the object to a learning network model configured to estimate a scatter radiation-processed medical image, when the X-ray apparatus operates, wherein the learning network model configured to estimate the scatter radiation-processed medical image is a learning network model taught using a plurality of original radiation images and a plurality of pieces of capturing condition information related to each of the plurality of original radiation images.

In accordance with another aspect of the present disclosure, a computer program product including computer-readable recording media includes instructions enabling an X-ray apparatus to acquire an original radiation image of a target object and capturing condition information of the object, to acquire a scatter radiation image related to the original radiation image by inputting the original radiation image and the capturing condition information to a learning network model configured to estimate scatter radiation, and to acquire a scatter radiation-processed medical image from the original radiation image on the basis of the original radiation image and the scatter radiation image, wherein the learning network model configured to estimate scatter radiation is a learning network model taught using a plurality of scatter radiation images and a plurality of pieces of capturing condition information related to each of the plurality of scatter radiation images.

In accordance with another aspect of the present disclosure, a computer program product including computer-readable recording media includes instructions enabling an X-ray apparatus to acquire an original radiation image of a target object and capturing condition information of the object, and acquire a scatter radiation-processed medical image from the original radiation image by inputting the original radiation image and the capturing condition information to a learning network model configured to estimate the scatter radiation-processed medical image, wherein the learning network model configured to estimate the scatter radiation-processed medical image may be a learning network model taught using a plurality of original radiation images and a plurality of pieces of capturing condition information related to each of the plurality of original radiation images.

In an aspect of the present disclosure, there is a method of acquiring a medical image of an X-ray apparatus performed by one or more computers, the method including: acquiring an original radiation image of an object and capturing condition information of the object; acquiring a scatter radiation image related to the original radiation image by inputting the original radiation image and the capturing condition information to a learning network model configured to estimate scatter radiation; and outputting a scatter radiation-processed medical image from the original radiation image based on the original radiation image and the scatter radiation image, the scatter radiation-processed medical image having less scatter radiation information than the original radiation image, wherein the learning network model configured to estimate scatter radiation includes a learning network model taught based on a plurality of scatter radiation images and a plurality of pieces of capturing condition information related to a plurality of scatter radiation images.

In yet another aspect of the present disclosure, there is a method of acquiring a medical image of an X-ray apparatus performed by one or more computers, the method including: acquiring an original radiation image of a target object and capturing condition information of the target object; and acquiring a scatter radiation-processed medical image from the original radiation image by inputting the original radiation image and the capturing condition information to a learning network model configured to estimate a scatter radiation-processed medical image, wherein the learning network model configured to estimate a scatter radiation-processed medical image is a learning network model taught based on a plurality of original radiation images and a plurality of pieces of capturing condition information related to each of the plurality of original radiation images.

In one aspect of the present disclosure, there is an X-ray apparatus including: an X-ray emitter configured to emit X-rays toward an object; an X-ray detector configured to detect the X-rays that have passed through the object; a controller communicatively connected to the X-ray emitter and the X-ray detector to control the X-ray apparatus; and a memory communicatively connected to the controller, wherein the memory is configured to store instructions for the controller to perform a control operation to: acquire a scatter radiation image related to an original radiation image of the object acquired from the X-ray detector, by inputting the original radiation image and capturing condition information of the object to a learning network model configured to estimate scatter radiation, and acquire a scatter radiation-processed medical image from the original radiation image based on the original radiation image and the scatter radiation image, and wherein the learning network model configured to estimate scatter radiation includes learning network model taught based on a plurality of scatter radiation images and a plurality of pieces of capturing condition information related to the plurality of scatter radiation images.

In another aspect of the present disclosure, there is an X-ray apparatus including: an X-ray emitter configured to emit X-rays toward an object; an X-ray detector configured to detect the X-rays that have passed through the object; a controller communicatively connected to the X-ray emitter and the X-ray detector to control the X-ray apparatus; and a memory communicatively connected to the controller. The memory is configured to store instructions for the controller to perform a control operation to acquire a scatter radiation-processed medical image from an original radiation image of the object acquired from the X-ray detector, the scatter radiation-processed medical image being acquired by inputting the original radiation image and capturing condition information of the object to a learning network model configured to estimate a scatter radiation-processed medical image. Further, the learning network model configured to estimate the scatter radiation-processed medical image includes a learning network model taught based on a plurality of original radiation images and a plurality of pieces of capturing condition information related to the plurality of original radiation images.

In yet another aspect of the present disclosure, there is a computer program product including computer-readable recording media, the computer program product including instructions enabling an X-ray apparatus to: acquire an original radiation image of an object and capturing condition information of the object, acquire a scatter radiation image related to the original radiation image by inputting the original radiation image and the capturing condition information to a learning network model configured to estimate scatter radiation, and acquire a scatter radiation-processed medical image from the original radiation image based on the original radiation image and the scatter radiation image. The learning network model configured to estimate scatter radiation includes a learning network model taught based on a plurality of scatter radiation images and a plurality of pieces of capturing condition information related to the plurality of scatter radiation images.

BRIEF DESCRIPTION OF THE DRAWINGS

These and/or other aspects of the disclosure will become apparent and more readily appreciated from the following description of the exemplary embodiments, taken in conjunction with the accompanying drawings of which:

FIGS. 14 and 15 are flowcharts illustrating a method of acquiring a medical image using an X-ray apparatus according to an exemplary embodiment of the present disclosure.

DETAILED DESCRIPTION

Figure 1:
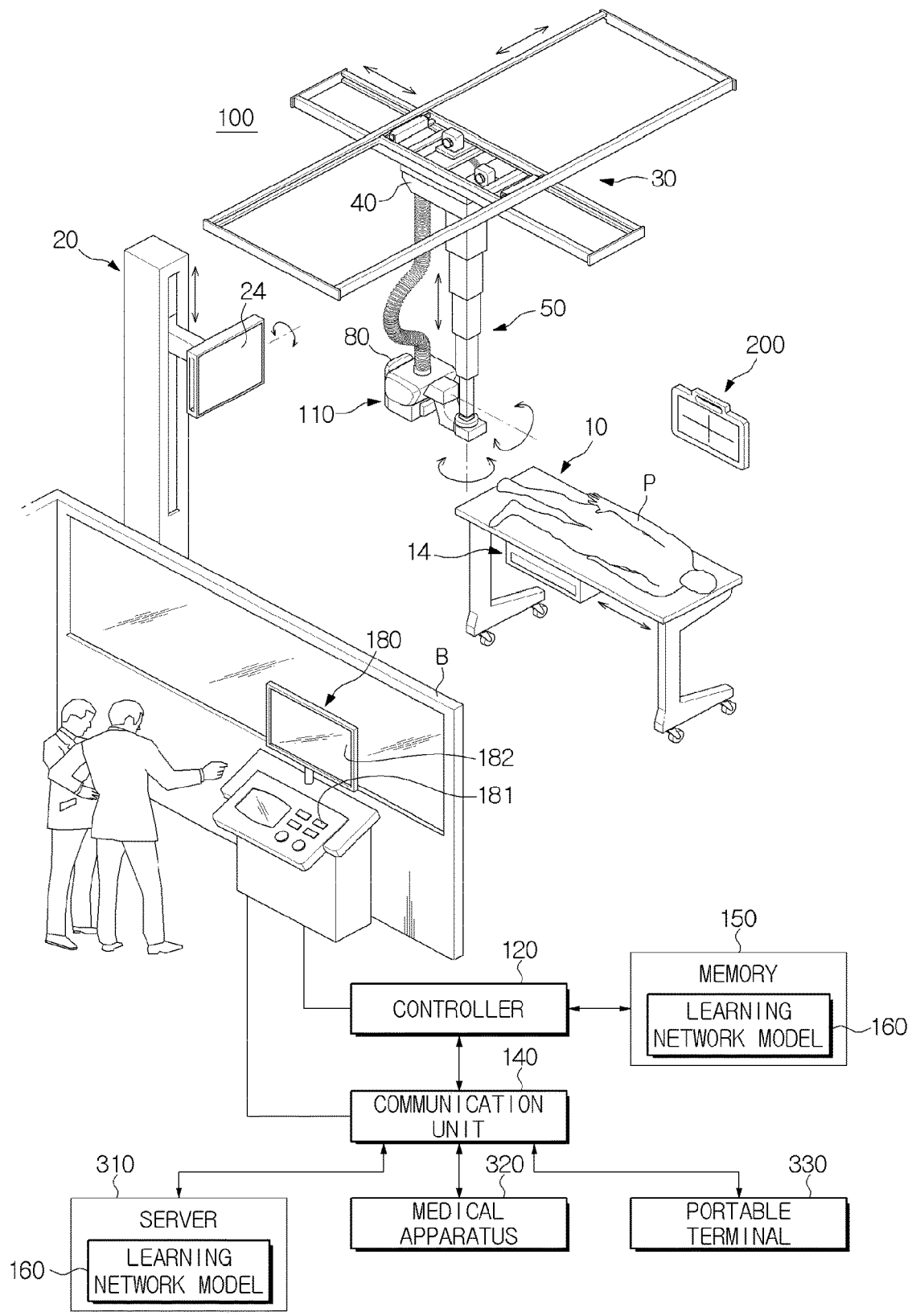
FIG. 1 is a view illustrating a structure of an X-ray apparatus according to an exemplary embodiment of the present disclosure.

Reference will now be made in detail to the exemplary embodiments of the present disclosure, examples of which are illustrated in the accompanying drawings, wherein like reference numerals refer to like elements throughout.

In the present specification, the principle of the present disclosure is explained and exemplary embodiments thereof are disclosed in such a manner that the scope of the present disclosure should become apparent and the present disclosure may be carried out by one of ordinary skill in the art to which the present disclosure pertains. The exemplary embodiments set forth herein may be implemented in many different forms.

Like reference numerals refer to like elements throughout the specification. The present specification does not describe all elements of exemplary embodiments, and general content in the art to which the present disclosure pertains or identical content between exemplary embodiments will be omitted. The terms "part" and "portion" as used herein may be embodied as software or hardware, and a plurality of "parts" may be embodied as a single unit or element, while a single "part" may include a plurality of elements, according to exemplary embodiments. Hereinafter, an operating principle and exemplary embodiments of the present disclosure will be described with reference to the accompanying drawings. The expression, "at least one of a, b, and c," should be understood as including only a, only b, only c, both a and b, both a and c, both b and c, or all of a, b, and c.

In the present specification, an image may include a medical image acquired by a medical imaging apparatus such as a magnetic resonance imaging (MRI) apparatus, a computerized tomography (CT) imaging apparatus, an ultrasonic imaging apparatus, an X-ray imaging apparatus, or the like.

The term "object" as used herein refers to an object to be imaged, and may include, for example, a human, an animal, or a part thereof. For example, the object may include a part of a body (e.g., an organ), a phantom, or the like.

FIG. 1 is a view illustrating a structure of an X-ray apparatus 100 according to an exemplary embodiment of the present disclosure. FIG. 1 exemplarily illustrates a fixed-type X-ray apparatus.

Referring to FIG. 1, the X-ray apparatus 100 includes an X-ray emitter 110 configured to generate and emit X-rays, an X-ray detector 200 configured to detect X-rays emitted from the X-ray irradiator 110 and passed through an object, and a work station 180 configured to receive commands from a user and provide information to the user. In addition, the X-ray apparatus 100 may include a controller 120 configured to control the X-ray apparatus 100 according to the input commands and a communication unit 140 configured to communicate with an external device.

Elements of the controller 120 and the communication unit 140 may be partially or completely included in the work station 180 or may be separately arranged from the work station 180 (e.g., in a separate server).

The X-ray emitter 110 may include an X-ray source configured to generate X-rays, and a collimator configured to control an irradiation region of the X-rays generated from the X-ray source.

Guide rails 30 may be installed on the ceiling of an inspection room where the X-ray apparatus 100 is located, the X-ray emitter 110 may be connected to a moving carriage 40 configured to move along the guide rails 30 to move the X-ray emitter 110 to a position corresponding to an object P, and the moving carriage 40 and the X-ray emitter 110 may be connected to each other via an extendable or telescoping post frame 50 to adjust a height of the X-ray emitter 110.

The work station 180 may include an input unit 181 configured to receive commands of a user and a display unit 182 configured to display information.

The input unit 181 may receive commands for a capturing protocol, capturing condition information, a capturing timing, controlling a position of the X-ray emitter 110, and the like. The input unit 181 may include a keyboard, a mouse, a touchscreen, a speech recognizer, and the like.

The display unit 182 may display a screen for guiding or receiving input of a user, an X-ray image, a screen displaying a state of the X-ray apparatus 100, or the like.

The controller 120 may control the capturing timing, the capturing condition information, or the like of the X-ray emitter 110 according to a command input from a user, and may produce a medical image using image data received from the X-ray detector 200. In addition, the controller 120 may control a position or posture of the x-ray emitter 110 or installation parts 14 and 24 at which the X-ray detector 200 is installed, or both. In an alternative exemplary embodiment, the x-ray emitter 110 is installed at the installation parts 14 or 24, and the controller 120 may control a position of the installation parts 14 or 24, or control a position of an X-ray detector 200 that is installed at another position.

The controller 120 may include a memory configured to store a program for executing the above-described operation and an operation that will be described below, and at least one processor configured to execute the stored program, and may be arranged in the work station 180. The controller 120 may include a single processor, or a plurality of processors. In the latter case, the plurality of processors may be integrated on a single chip, or may be physically separated from each other.

When the controller 120 includes a plurality of processors, some of the processors may be arranged in the work station 180, and some of the processors may be arranged in a sub-user interface (UI) 80, the moving carriage 40, or other devices. For example, the processor arranged in the work station 180 may perform control of imaging or the like for producing a medical image, and the processor arranged in the sub-UI 80 or the moving carriage 40 may perform control related to movement of the X-ray emitter 110 or the X-ray detector 200.

The X-ray apparatus 100 may be wiredly or wirelessly connected to an external device (e.g., an external server 310), a medical apparatus 320, and a portable terminal 330 (e.g., a smartphone, a tablet PC, a wearable device, or the like) via the communication unit 140 to transmit or receive data therewith.

The communication unit 140 may include one or more elements configured to enable communication with an external device, and may include, for example, at least one of a short-range communication module, a wired communication module, and a wireless communication module.

In addition, the communication unit 140 may receive a control signal from an external device, and transmit the received control signal to the controller 120 to enable the controller 120 to control the X-ray apparatus 100 according to the received control signal.

In addition, the controller 120 may transmit or receive a control signal to or from an external device via the communication unit 140 to control the external device according to the control signal of the controller 120. For example, the external device may process data according to the control signal of the controller 120 received via the communication unit 140.

In addition, the communication unit 140 may further include an internal communication module configured to enable communication between elements of the X-ray apparatus 100. A program capable of controlling the X-ray apparatus 100 may be installed at an external device such that the program may include a command configured to partially or completely perform operations of the controller 120.

The program may be previously installed in the portable terminal 330, or a user of the portable terminal 330 may install the program by downloading the program from an application providing server. The application providing server may include recording media storing the corresponding program.

Meanwhile, the X-ray detector 200 may be embodied as a fixed-type X-ray detector fixed on a stand 20 or a table 10, may be detachably installed at the installation parts 14 and 24, or may be embodied as a portable X-ray detector usable at an arbitrary position. The portable X-ray detector may be a wired type X-ray detector or a wireless type X-ray detector according to a data transmission method and a power supply method thereof.

The X-ray detector 200 may be included or not included as a element of the X-ray apparatus 100. In the latter case, the X-ray detector 200 may be registered in the X-ray apparatus 100 by a user. In addition, in both cases, the X-ray detector 200 may be connected to the controller 120 via the communication unit 140 to receive a control signal therefrom or transmit image data thereto.

The sub-UI 80 configured to provide a user with information and receive a command from the user may be provided at a side surface of the X-ray emitter 110, and functions performed by the input unit 181 and the display unit 182 of the work station 180 may be partially or completely performed in the sub-UI 80.

Although FIG. 1 illustrates the fixed-type X-ray apparatus connected to the ceiling of an inspection room, the X-ray apparatus 100 may include X-ray apparatuses having a variety of structures within a range obvious to one of ordinary skill in the art, a C-arm-type X-ray apparatus, a mobile X-ray apparatus, and the like.

Figure 2:
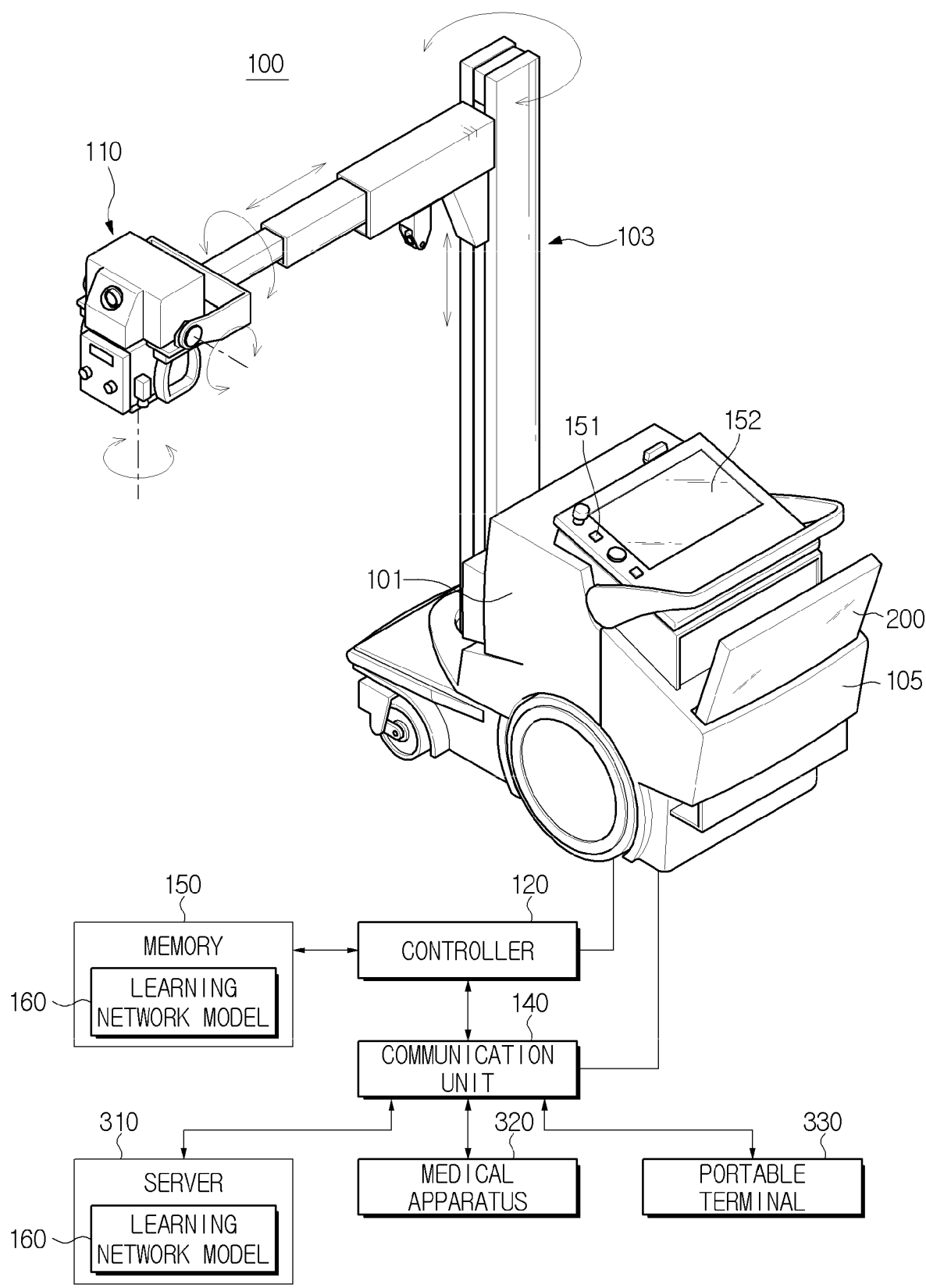
FIG. 2 is a view illustrating a structure of a mobile X-ray apparatus according to an exemplary embodiment of the present disclosure.

FIG. 2 is a view illustrating a mobile X-ray apparatus as an example of an X-ray apparatus.

The same reference numerals as those in FIG. 1 perform the same functions, and thus detailed descriptions thereof will be omitted herein.

The X-ray apparatus 100 may be embodied as the above-described ceiling type X-ray apparatus or a mobile type X-ray apparatus. When the X-ray apparatus 100 is embodied as a mobile X-ray apparatus, a main body 101 connected to the X-ray emitter 110 is freely movable and an arm 103 connecting the X-ray emitter 110 to the main body 101 is also rotatable and linearly movable, and thus the X-ray emitter 110 may be freely movable in a three-dimensional space.

The main body 101 may include a storage part 105 configured to store the X-ray detector 200. In addition, a charging terminal capable of charging the X-ray detector 200 may be provided inside the storage part 105 such that the storage part 105 may store and charge the X-ray detector 200.

An input unit 151, a display unit 152, the controller 120, and the communication unit 140 may be arranged in the main body 101, and image data acquired by the X-ray detector 200 may be transmitted to the main body 101, undergo image processing, and then be displayed on the display unit 152, or may be transmitted to an external device via the communication unit 140.

In addition, the controller 120 and the communication unit 140 may be separately arranged from the main body 101, or only a part of elements of the controller 120 and the communication unit 140 may be arranged in the main body 101.

The memory 150 of each of the X-ray apparatuses 100 of FIGS. 1 and 2 may be configured to store a learning network model 160 according to an exemplary embodiment of the present disclosure.

The learning network model 160 may be designed such that a brain structure of a human is simulated on the computer or at least one processor.

For example, the learning network model 160 may include a plurality of network nodes having weights and simulating neurons of a human neural network. The plurality of network nodes may form a connection relationship therebetween to simulate a synaptic event for signal transduction via a synapse.

The learning network model 160 may include, for example, an artificial intelligence (AI) neural network model or a deep learning network model developed from the neural network model. In the deep learning network model, a plurality of network nodes may be located at different depths (or layers) thereof and transmit or receive data according to a convolution connection relationship.

The learning network model 160 may be embodied as, for example, a software module. When the learning network model 160 is embodied as a program (module) including a software module (e.g., an instruction), the learning network model 160 may be stored in computer readable recording media. In this case, the computer readable recording media may be at least a part of the memory 150 of the X-ray apparatus 100 of FIG. 1.

In another exemplary embodiment, the learning network model 160 may be integrated in the form of a hardware chip, and thus may be a part of the above-described controller 120. For example, the learning network model 160 may be designed in the form of an exclusive hardware chip for AI, or may be designed as a part of an existing general purpose processor (e.g., a central processing unit (CPU) or an application processor) or a graphic exclusive processor (e.g., a graphics processing unit (GPU)).

In another exemplary embodiment, the learning network model 160 may be designed in the form of a software module or a hardware chip and be located in the external server 310.

In yet another exemplary embodiment, the learning network model 160 may be embedded software or may be firmware that may or may not run in conjunction with an operating system.

In this case, the X-ray apparatus 100 may transmit input data for image processing to the external server 310 via the communication unit 140. The input data may include, for example, an original radiation image detected by the X-ray apparatus 100. The original radiation image may indicate an entire radiation image based on radiation incident on the X-ray detector 200. The original radiation image may also be referred to as, for example, a primarily processed radiation image, an initial radiation image, or a raw radiation image.

The external server 310 may input the input data received from the X-ray apparatus 100 to the learning network model 160 to acquire an improved medical image, and may transmit the acquired medical image to the communication unit 140 of the X-ray apparatus 100.

When the learning network model 160 located in the external server 310 is embodied as a software module, the learning network model 160 may be stored in computer readable recording media. In this case, the computer readable recording media may be a memory (not shown) of the server 310 of FIG. 1.

The learning network model 160 may be produced in the external server 310. The external server 310 may be, for example, a server of a manufacturer of the X-ray apparatus 100, a server of an administrator of the X-ray apparatus 100, or a third-party server commissioned or leased by the manufacturer or the administrator. The external server 310 may be a server configured only to generate or update the learning network model 160, or may be a server configured to receive input data from the X-ray apparatus 100 and provide an improved image processed using the learning network model 160.

The external server 310 may teach the learning network model 160 using learning data. The learning data may be, for example, at least one of an original radiation image captured by the X-ray apparatus 100 or another X-ray apparatus, a scatter image concerning the original radiation image, and a medical image on which scatter radiation treatment is performed.

The learning data may be collected by the manufacturer or administrator of the X-ray apparatus 100 from a hospital or a doctor, or results obtained using the learning network model 160 in the X-ray apparatus 100 may be reused as learning data.

The learning network model 160 may be periodically or non-periodically updated. A case of non-periodical updating may include, for example, a case in which there is an administrator request or a case in which a certain capacity or more of learning data is collected.

According to various exemplary embodiments, a process of producing the learning network model 160 may be performed directly in the X-ray apparatus 100. That is, the X-ray apparatus 100 may perform teaching and updating of the learning network model 160 as well as image processing using the learning network model 160.

In addition, the external server 310 may include a plurality of servers. The plurality of servers may include, for example, a cloud server. The cloud server may include a system configured to store and process data using resources of a variety of devices (servers, clients, or the like) connected to each other in an Internet environment.

According to an exemplary embodiment of the present disclosure, the learning network model 160 may be configured to estimate a scatter radiation image or to estimate a medical image obtained by processing scatter radiation from the original radiation image. In another exemplary embodiment, the learning network model 160 may be configured to estimate a bone structure radiation image.

Examples of estimating a scatter radiation image, a medical image on which scatter radiation is processed, and a bone structure radiation image using the learning network model 160 will be described below in detail, and detailed descriptions of the same elements will be omitted.

Meanwhile, in the present disclosure, when the learning network model 160 is used to estimate a scatter image, the learning network model 160 is regarded as indicating an integrated form of a plurality of scatter kernels instead of using each of a plurality of existing scatter kernels, and thus may be referred to as an integrated scatter network model.

The expression "the learning network model 160 is configured to achieve the above-described goal" as used herein may mean that the learning network model 160 is not a general learning network model capable of responding to a variety of cases, but is a learning network model taught for a specific purpose and, accordingly, is implemented in accordance with the purpose.

Figure 3:
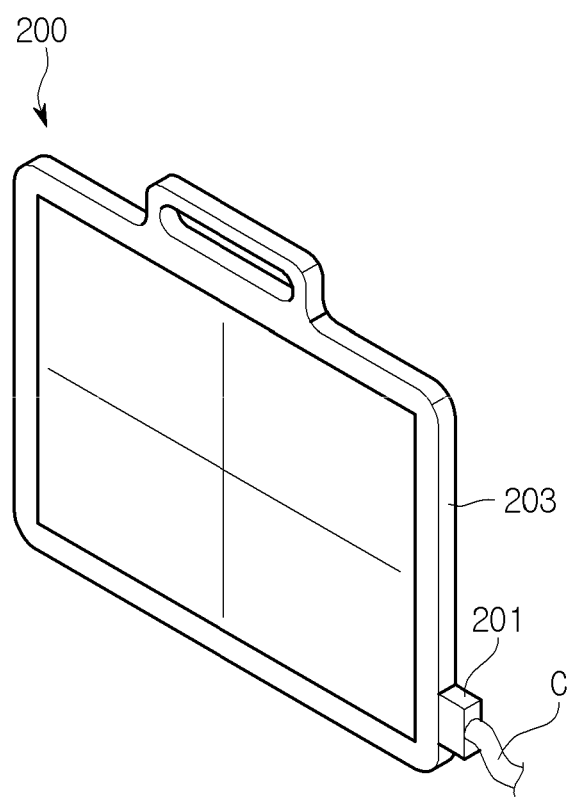
FIG. 3 is a view of an exterior of a portable X-ray detector according to an exemplary embodiment of the present disclosure.

FIG. 3 is a view of an exterior of a portable X-ray detector.

As described above, the X-ray detector 200 used in the X-ray apparatus 100 may be embodied as a portable X-ray detector. In this case, the X-ray detector 200 may include a battery configured to supply electric power to be operated in a wireless manner. As illustrated in FIG. 3, a charging port 201 may be connected to a separate power supply via a cable C to be operated.

A detection element configured to detect X-rays and convert the X-rays into image data, a memory configured to temporarily or non-temporarily store the image data, a communication module configured to receive a control signal from the X-ray apparatus 100 or transmit image data to the X-ray apparatus 100, and a battery may be provided in a case 203 which forms an external appearance of the X-ray detector 200. In addition, the memory may store image correction information of the X-ray detector 200 and unique identification information of the X-ray detector 200, and may also transmit identification information stored therein when communicating with the X-ray apparatus 100.

Figure 4:
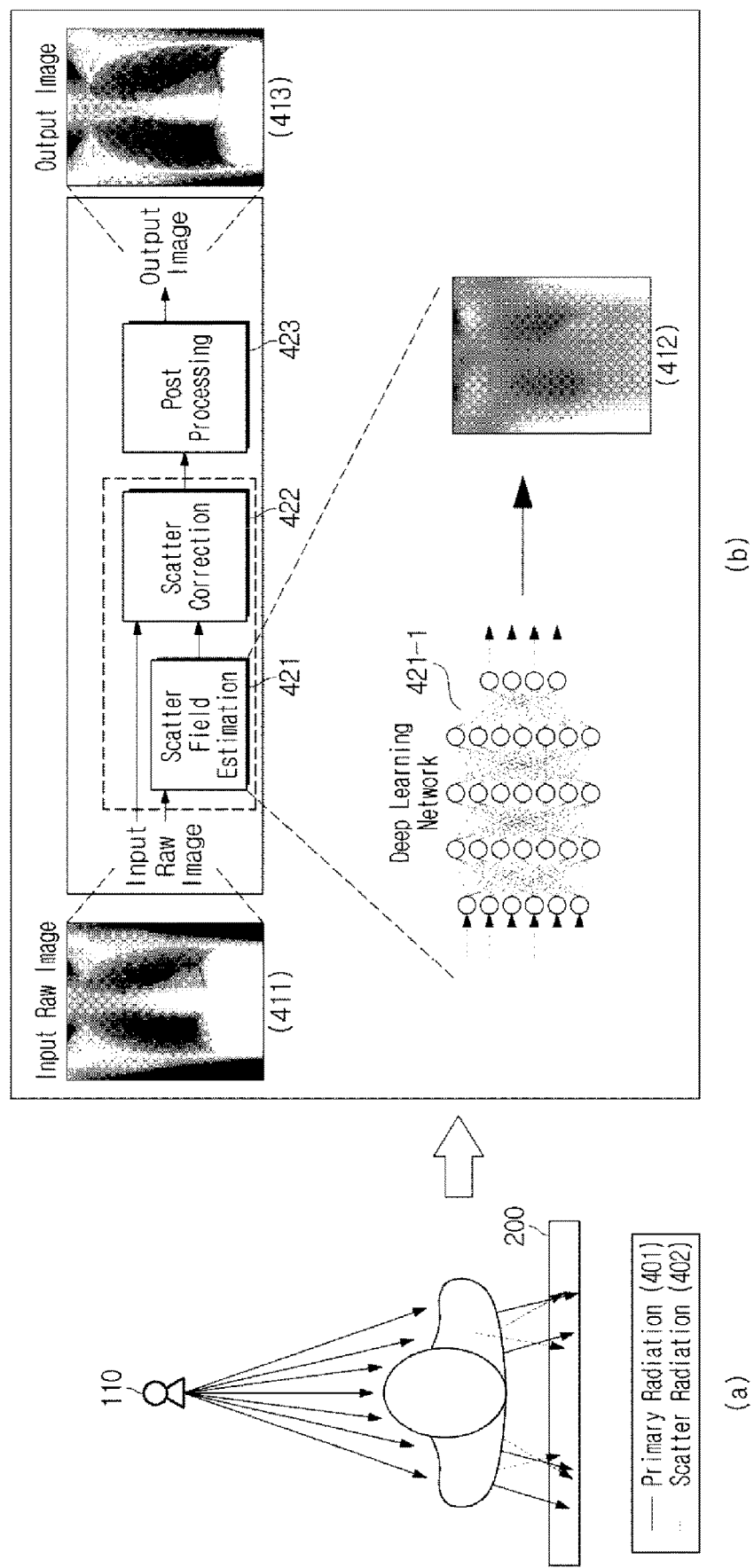
FIG. 4 is a view illustrating a process of acquiring a medical image using an X-ray apparatus according to an exemplary embodiment of the present disclosure.

FIG. 4 is a view illustrating a process of acquiring a medical image using an X-ray apparatus according to an exemplary embodiment of the present disclosure.

Referring to (a) of FIG. 4, when the X-ray emitter 110 irradiates an object with X-rays, the X-ray detector 200 may detect radiation passed through the object. Radiation incident on the X-ray detector 200 may include primary radiation 401 including important information and scatter radiation 402 which degrades the quality of an image.

The X-ray detector 200 may transmit original image data generated according to the primary radiation 401 and the scatter radiation 402 to the work station 180 or the main body 101.

When the work station 180 or the main body 101 receives the original radiation image, the original radiation image may be subjected to scatter radiation processing to acquire a medical image.

In particular, referring to (b) of FIG. 4, when an original radiation image 411 is acquired from the X-ray detector 200, the X-ray apparatus 100 may perform scatter field estimation 421. In this case, the X-ray apparatus 100 may perform the scatter field estimation 421 using a learning network model 421-1 configured to estimate radiation from which scatter is removed.

In this case, the learning network model 421-1 may include, for example, an AI neural network model or a deep learning network model. In addition, an estimation of scatter may include, for example, estimating at least one of a scatter field and scatter aggregate distributed in the original radiation image 411, a scatter density, a scatter distribution type, and a scatter dispersion.

When a scatter radiation image 412 is acquired through the scatter field estimation 421 using the learning network model 421-1, the X-ray apparatus 100 may perform scatter processing 422 (or scatter correction) by receiving the original radiation image 411 and the scatter radiation image 412 to acquire a scatter radiation processed medical image. In this regard, a scatter radiation processing process may include removing at least a portion of scatter radiation, degrading the intensity of at least a portion of the scatter radiation, or filtering at least a portion of the scatter radiation.

When the scatter processed radiation image is acquired, the X-ray apparatus 100 may acquire a final medical image 413 through post processing 423. In an exemplary embodiment the scatter processed radiation image has less scatter radiation than the original image. The post processing 423 may include, for example, a process of removing noise of an input image or a process of adjusting contrast of the input image.

The above-described process of acquiring a scatter processed radiation image may be shown by Equation 1 below.

[Equation 1]

$$P = w_p T - S(T)$$

T: total radiation(input image)
P: primary radiation
S(T): estimated scatter radiation
$w_p$: primary radiation ratio between In/Non-grid In Equation 1, T denotes an entire radiation image based on radiation incident on the X-ray detector 200. The entire radiation image may be referred to as an original radiation image or a raw radiation image.

The original radiation image may be a radiation image based on image data received from the X-ray detector 200 when a general anti-scatter grid is not used. Accordingly to various exemplary embodiments, however, a radiation image received from the X-ray detector 200 when an anti-scatter grid is used may be an object of the original radiation image.

S(T) denotes a scatter radiation image estimated through the above-described scatter estimation process.

$w_p$ denotes a weight of the original radiation image calculated in consideration of a difference between before and after the anti-scatter grid is inserted.

P denotes a primary radiation image including important information. According to Equation 1, the primary radiation image may be an image obtained by removing the estimated scatter radiation image from an entire weighted radiation image.

According to an exemplary embodiment of the present disclosure, the X-ray apparatus 100 may use an algorithm and application capable of accurately estimating scatter to actively respond to a variety of pieces of image capturing condition information and characteristics of an object.

In particular, the X-ray apparatus 100 of the present disclosure may estimate scatter using a learning network model (e.g., a deep learning network model). In another exemplary embodiment, the X-ray apparatus 100 of the present disclosure may estimate a scatter-removed radiation image using a deep learning network model. In another exemplary embodiment, the X-ray apparatus 100 of the present disclosure may directly estimate a scatter-removed and post processed medical image using a deep learning network model.

According to various exemplary embodiments, an estimation of a medical image may be performed using exemplary embodiments of the present disclosure and existing exemplary embodiments. For example, a scatter-removed radiation image may be acquired using different scatter kernels according to a region or thickness of a body site. In addition, the scatter-removed radiation image may be input back to the learning network model of the present disclosure to acquire a radiation image from which a greater amount of scatter is removed.

Hereinafter, a process of producing a learning network model (e.g., a deep learning network model) and acquiring a radiation image using the generated learning network model, according to various exemplary embodiments of the present disclosure, will be described.

Figure 5:
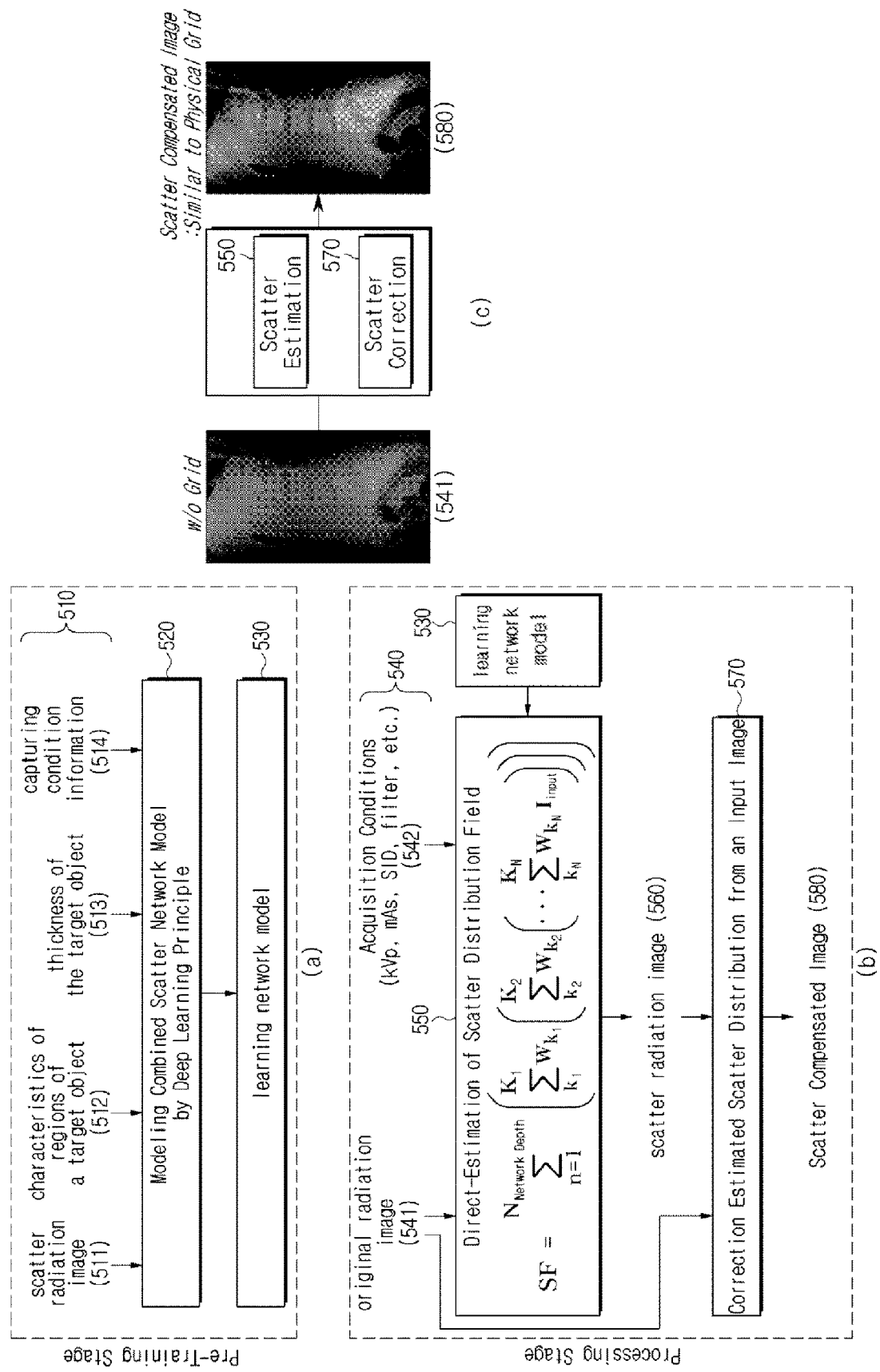
FIGS. 5 to 7 are views illustrating a process of acquiring a medical image by applying a learning network model to an X-ray apparatus according to an exemplary embodiment of the present disclosure.

FIG. 5 is a view illustrating a process of acquiring a medical image using a learning network model (e.g., a deep learning network model) according to an exemplary embodiment of the present disclosure.

In FIG. 5, (a) illustrates a process of producing a learning network model and (b) illustrates a process of acquiring a radiation image using the learning network model.

First, referring to (a) of FIG. 5, a modeling process 520 of teaching a learning network model may be performed based on learning data 510 including a scatter radiation image. In this case, the learning data 510 may include, for example, at least one of a scatter radiation image 511, characteristics of regions of a target object 512, a thickness of the target object 513, and capturing condition information 514. The capturing condition information 514 may include, for example, at least one of kVp, mAs, SID, and filter. In this regard, kVp and mAs refer to voltage and current, respectively, applied to an X-ray emitter to generate X-rays, SID denotes a distance from a tube of the X-ray emitter to the object, and filter may represent a range of an energy band of emitted X-rays.

In addition, the learning data 510 may include an original radiation image.

When the modeling process 520 is completed, as a result, a learning network model 530 configured to estimate scatter radiation may be obtained.

Referring to (b) of FIG. 5, when the learning network model 530 (e.g., a combined scatter network model) is obtained, the X-ray apparatus 100 may perform scatter radiation image estimation 550 (e.g., direct-estimation of scatter distribution field) in which input data 540 (e.g., acquisition conditions (kVp, mAs, SID, filter, etc.) is applied to the learning network model 530 configured to estimate scatter radiation. As a result, the X-ray apparatus 100 may acquire a scatter radiation image 560. In this case, the input data 540 may include, for example, an original radiation image 541 acquired when an anti-scatter grid is not used, and capturing condition information 542.

In particular, the X-ray apparatus 100 may acquire the scatter radiation image 560 by summing results obtained by applying weights of network nodes to the input data 540 according to each of a plurality of network depths.

The above-described process of acquiring the scatter radiation image 560 using the X-ray apparatus 100 is shown by Equation 2 below.

$$SF = \sum_{n=1}^{N_{Network Depth}} \left( \sum_{k_1}^{K_1} W_{k_1} \left( \sum_{k_2}^{K_2} W_{k_2} \left( \ldots \sum_{k_N}^{K_N} W_{k_N} I_{input} \right) \right) \right) \qquad \text{[Equation 2]}$$

In Equation 2, SF denotes the estimated scatter radiation image 560.

W denotes weights of network nodes of the learning network model 530 configured to estimate scatter radiation, and $I_{input}$ denotes the input data 540.

Next, the X-ray apparatus 100 may perform scatter processing 570 (e.g., correction estimated scatter distribution from an input image) in which the estimated scatter radiation image 560 is removed (or corrected) from the original radiation image 541.

As a result of the scatter processing 570, the X-ray apparatus 100 may acquire a scatter radiation-processed (or compensated) medical image 580.

In FIG. 5, (c) illustrates radiation images before and after application of the above-described process.

Referring to (c) of FIG. 5, the X-ray apparatus 100 may perform the scatter radiation image estimation 550 and the scatter processing 570 (e.g., scatter correction) on the original radiation image 541 acquired when an anti-scatter grid is not used. As a result, the X-ray apparatus 100 may acquire the scatter radiation-processed medical image 580 (e.g., scatter compensated image). In this case, the scatter radiation-processed medical image 580 may be similar to an original radiation image from which scatter radiation is removed using an anti-scatter grid.

Figure 6:
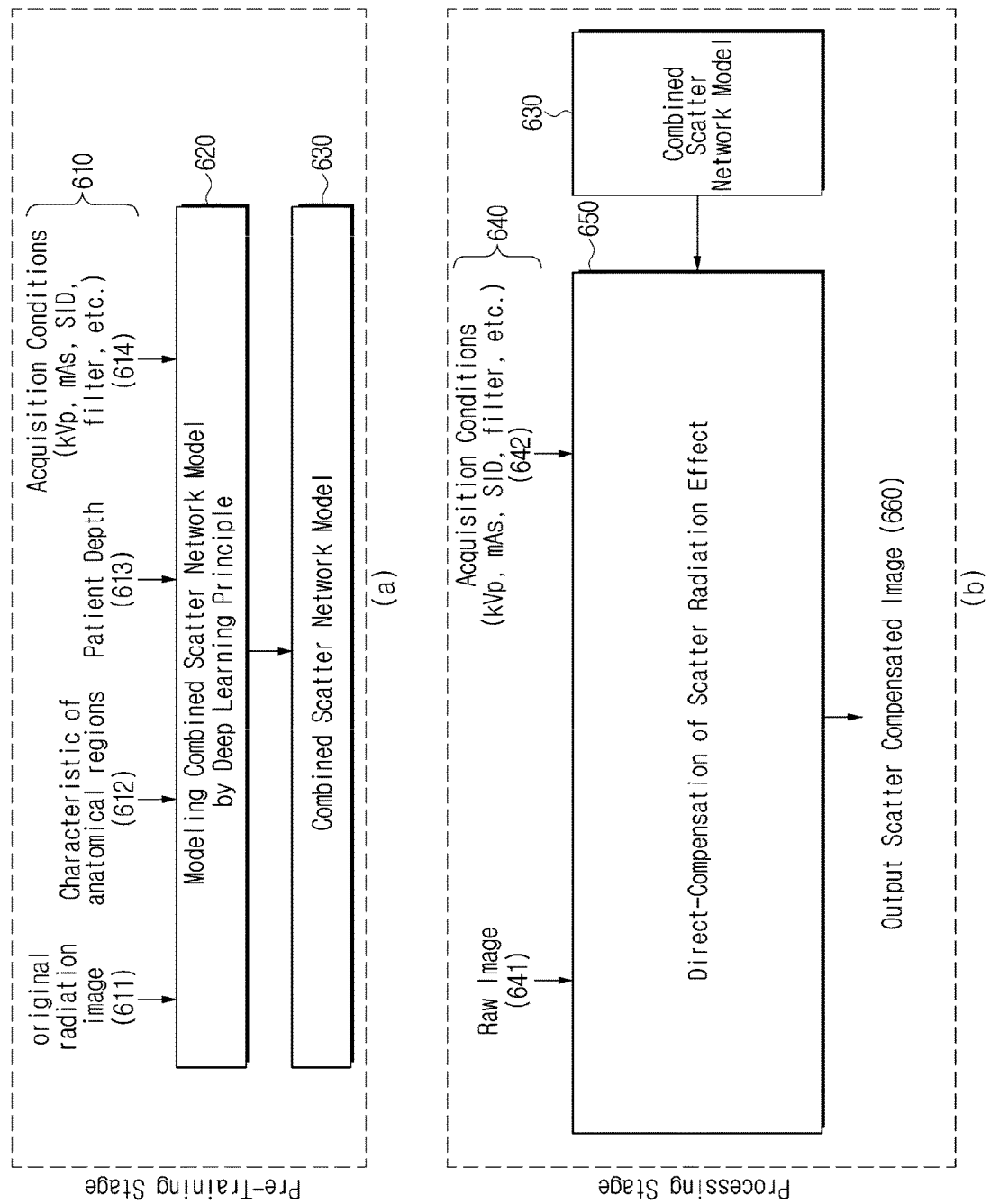

FIG. 6 illustrates diagrams illustrating a process of acquiring a medical image using a learning network model, according to another exemplary embodiment of the present disclosure.

First, referring to (a) of FIG. 6, a modeling process 620 (e.g., modeling combined scatter network model by deep learning principle) of teaching a learning network model may be performed based on learning data 610 including an original radiation image. In this case, the learning data 610 may include, for example, at least one of an original radiation image 611, characteristics of regions of a target object 612 (e.g., characteristics of anatomical regions), a thickness of the target object 613 (e.g., patent depth), and capturing condition information 614 (e.g., acquisition conditions such as kVp, mAs, SID, filter, etc.).

As a result of performing the modeling process 620, a learning network model 630 (e.g., combined scatter network model) configured to estimate a scatter radiation-processed medical image may be obtained.

Referring to (b) of FIG. 6, when the learning network model 630 is obtained, the X-ray apparatus 100 may perform scatter radiation image estimation 650 (e.g., direct-compensation of scatter radiation effect) in which input data 640 (e.g., raw image 641 and acquisition conditions 642) is applied to the learning network model 630 configured to estimate scatter radiation. As a result, the X-ray apparatus 100 may acquire a scatter radiation-processed (or compensated) medical image 660 (e.g., output scatter compensated image).

Figure 7:
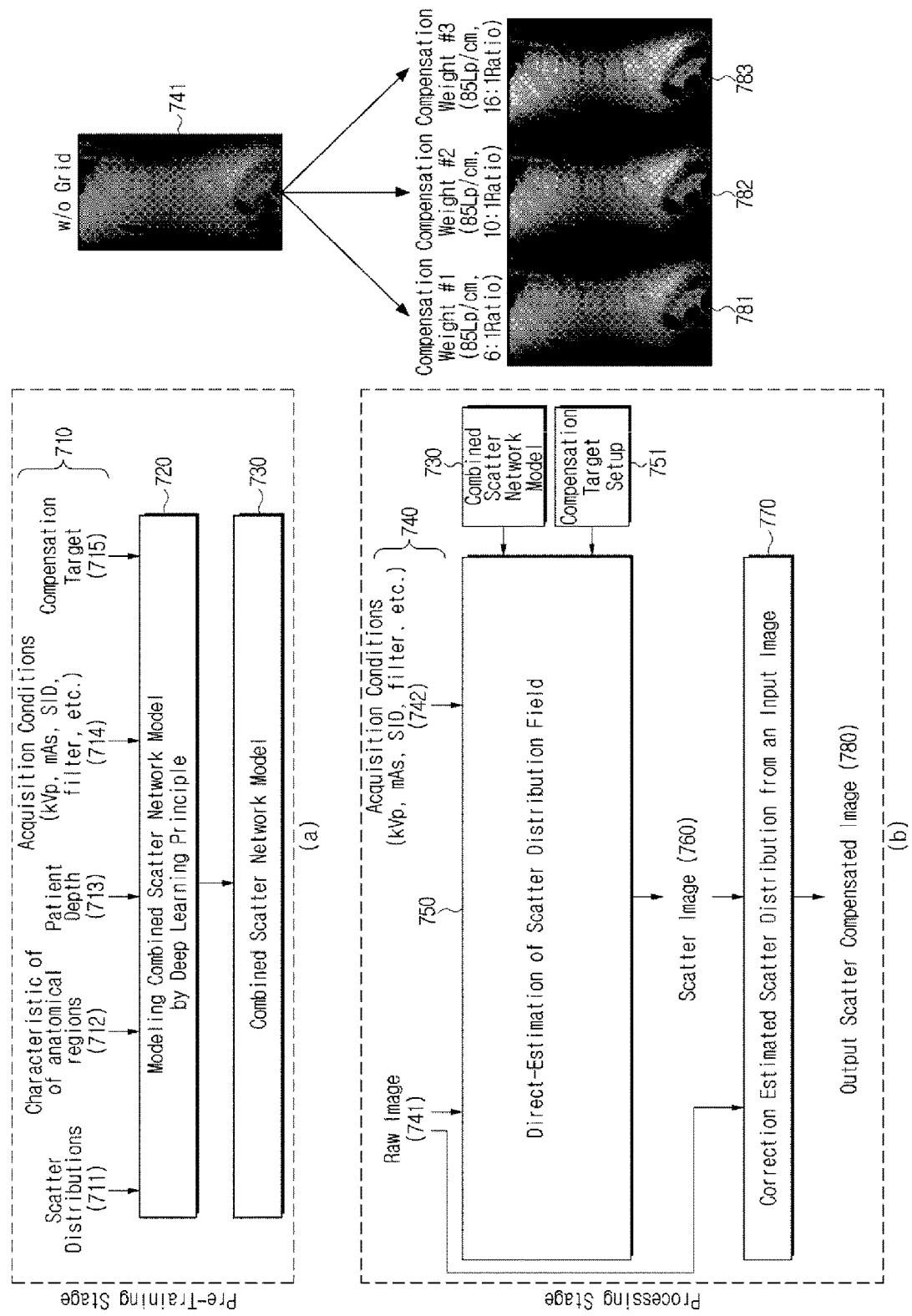

FIG. 7 illustrates a process of acquiring a medical image using a learning network model, according to an exemplary embodiment of the present disclosure.

In FIG. 7, a user of the X-ray apparatus 100 may desire to set a removal degree of scatter radiation for a medical image. For example, the user may desire a radiation image from which scatter radiation is completely removed, or a natural radiation image in which a certain degree of scatter radiation is included.

In this case, the X-ray apparatus 100 may provide a scatter radiation-processed medical image, based on the removal degree of scatter radiation from the scatter radiation image, selected by a user.

First, referring to (a) of FIG. 7, a modeling process 720 of teaching a learning network model may be performed based on learning data 710 including a scatter radiation image. In this case, the learning data 710 may include, for example, at least one of a scatter radiation image 711 (e.g., scatter distributions), characteristics of regions of a target object 712 (e.g., characteristics of anatomical regions), a thickness of the target object 713 (e.g., patient depth), capturing condition information 714 (e.g., acquisition conditions (kVp, mAs, SID, filter, etc.), and a degree of intensity (or compensation) of scatter radiation 715 (e.g., compensation target). In addition, the learning data 710 may also include an original radiation image.

In this regard, the removal degree of the scatter radiation image may include at least one of intensity, a distribution, and a density of scatter remaining in the original radiation image acquired after radiation passes through the anti-scatter grid. The removal degree of the scatter radiation image 711 may be determined by being manually set by an individual or by being automatically set according to an image processing technique. A value of the removal degree may be determined to be, for example, a value between 0 and 100.

As a result of performing the modeling process 720 (e.g., modeling combined scatter network model by deep learning principle), a learning network model 730 (e.g., combined scatter network model) configured to estimate a scatter radiation image may be obtained.

Referring to (b) of FIG. 7, when the learning network model 730 is obtained, the X-ray apparatus 100 may perform scatter radiation image estimation 750 (e.g., direct-estimation of scatter distribution field) in which input data 740 is applied to the learning network model 730 configured to estimate scatter radiation. As a result, the X-ray apparatus 100 may acquire a scatter radiation image 760. In this regard, the input data 740 may include, for example, an original radiation image 741 and capturing condition information 742 (e.g., acquisition conditions (kVp, mAs, SID, filter, etc.).

Meanwhile, a process 751 of setting a removal degree of scatter radiation (e.g., compensation target setup) may be further included in the scatter radiation image estimation 750 (e.g., direct-estimation of scatter distribution field). In this case, the X-ray apparatus 100 may acquire a scatter radiation image having a scatter radiation intensity corresponding to the set removal degree of scatter radiation. The process 751 (e.g., compensation target setup) of setting a removal degree of scatter radiation will be described below with reference to FIG. 8, and thus a detailed description thereof will be omitted Next, the X-ray apparatus 100 may perform scatter processing 770 (e.g., correction estimated scatter distribution from an input image) in which an estimated scatter radiation image 760 is removed from the original radiation image 741.

As a result of the scatter processing 770, based on the preset removal degree of scatter radiation, the X-ray apparatus 100 may acquire a medical image 780 (e.g., output scatter compensated image) having an intensity of scatter radiation corresponding to the removal degree.

In FIG. 7, (c) illustrates scatter radiation-processed medical images according to the preset removal degree of scatter radiation.

Referring to (c) in FIG. 7, the X-ray apparatus 100 may perform the scatter radiation image estimation 750 and the scatter processing 570 on the original radiation image 741. In this case, the X-ray apparatus 100 may acquire a medical image having an intensity of scatter radiation corresponding to the set removal degree of scatter radiation, according to the preset removal degree of scatter radiation. In this case, medical images may correspond to quality of a medical image acquired as a result of using an anti-scatter grid.

For example, when weight #1, e.g., compensation weight, is set as a value of the removal degree, a medical image 781 having the same or similar effect as that of an anti-scatter grid having "85 Lp/cm and 6:1 Ratio" may be acquired. In addition, when weight #2 is set as the value of the removal degree, a medical image 782 having the same or similar effect as that of an anti-scatter grid having "85 Lp/cm and 10:1 Ratio" may be acquired, and when weight #3 is set as the value of the removal degree, a medical image 783 having the same or similar effect as that of an anti-scatter grid having "85 Lp/cm and 16:1 Ratio" may be acquired. "Lp/cm" as used herein may refer to the number of pairs of grid lines included in 1 cm. In addition, the term "Ratio" as used herein may refer to a thickness of the anti-scatter grid. In this case, the greater the Lp/cm value, the higher clarity of a radiation image is, and a greater thickness of the anti-scatter grid may indicate a higher blocking rate of scatter radiation.

In this case, the specification of the above-described anti-scatter grid is merely an example, and a medical image having the same or similar effect as that of anti-scatter grids having a variety of specifications may be acquired according to the preset removal degree of scatter radiation.

Figure 8:
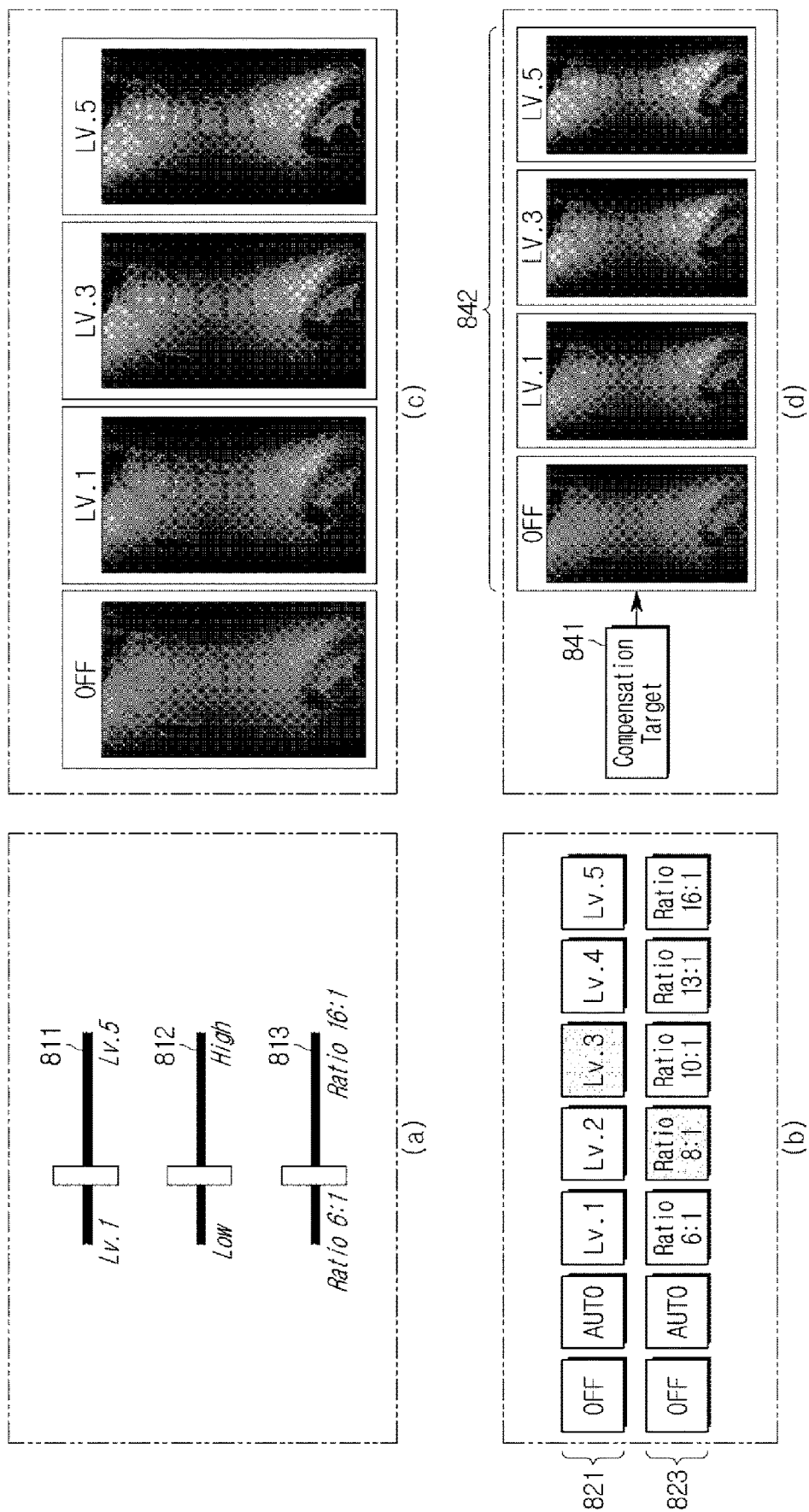
FIG. 8 illustrates a user interface (UI) configured to set a scatter radiation removal degree, according to an exemplary embodiment of the present disclosure.

FIG. 8 illustrates a UI configured to set a removal degree of scatter radiation, according to an exemplary embodiment of the present disclosure.

The UI configured to set the removal degree of scatter radiation may be provided, for example, via the input unit 181 or the display part 182 of the work station 180, or may be provided via the input unit 151 or the display part 152 of the mobile X-ray apparatus 100.

First, as illustrated in (a) of FIG. 8, the X-ray apparatus 100 may provide a scroll bar UI allowing a user to set the removal degree of scatter radiation. In this case, the removal degree of scatter radiation to be set by the user may be provided as level number slider, as illustrated in 811 of (a) of FIG. 8, may be provided as a high-to-low removal degree slider, as illustrated in 812 of (a) of FIG. 8, or may be provided as a thickness ratio slider, which is an example of specifications of the anti-scatter grid, as illustrated in 813 of (a) of FIG. 8.

In another exemplary embodiment, as illustrated in (b) of FIG. 8, the X-ray apparatus 100 may provide a button UI allowing a user to set the removal degree of scatter radiation. In this case, the removal degree of scatter radiation to be set by the user may be provided as level number, as illustrated in 821 of (b) of FIG. 8, or may be provided as a thickness ratio of the anti-scatter grid, as illustrated in 823 of (b) of FIG. 8.

In another exemplary embodiment, as illustrated in (c) of FIG. 8, the X-ray apparatus 100 may provide a button UI including thumbnail information to facilitate selection of a user. In this case, button UIs including thumbnail information may correspond to sample medical images having different removal degrees of scatter radiation.

In another exemplary embodiment, as illustrated in (d) of FIG. 8, the X-ray apparatus 100 may provide an UI configured to set a removal degree of scatter radiation in a stepwise manner. First, referring to (d) of FIG. 8, when a UI 841 configured to set the removal degree of scatter radiation is selected, the X-ray apparatus 100 may provide a plurality of button UIs corresponding to medical images having different intensities of scatter radiation in a stepwise manner.

In FIG. 8, as an example, a greater level number, a higher removal degree, and a larger thickness of the grid may indicate that a lower intensity of scatter radiation is shown in a medical image. That is, a clear medical image may be provided due to a high removal degree of scatter radiation. On the other hand, a smaller level number, a lower removal degree, and a smaller thickness of the grid may indicate that a higher intensity of scatter radiation is shown in a medical image. That is, a natural medical image similar to the original medical image may be provided due to a low removal degree of scatter radiation.

When a user sets the removal degree of scatter radiation using at least one of the provided UIs, the X-ray apparatus 100 may acquire a medical image having an intensity of scatter radiation corresponding to the set removal degree of scatter radiation.

Figure 9:
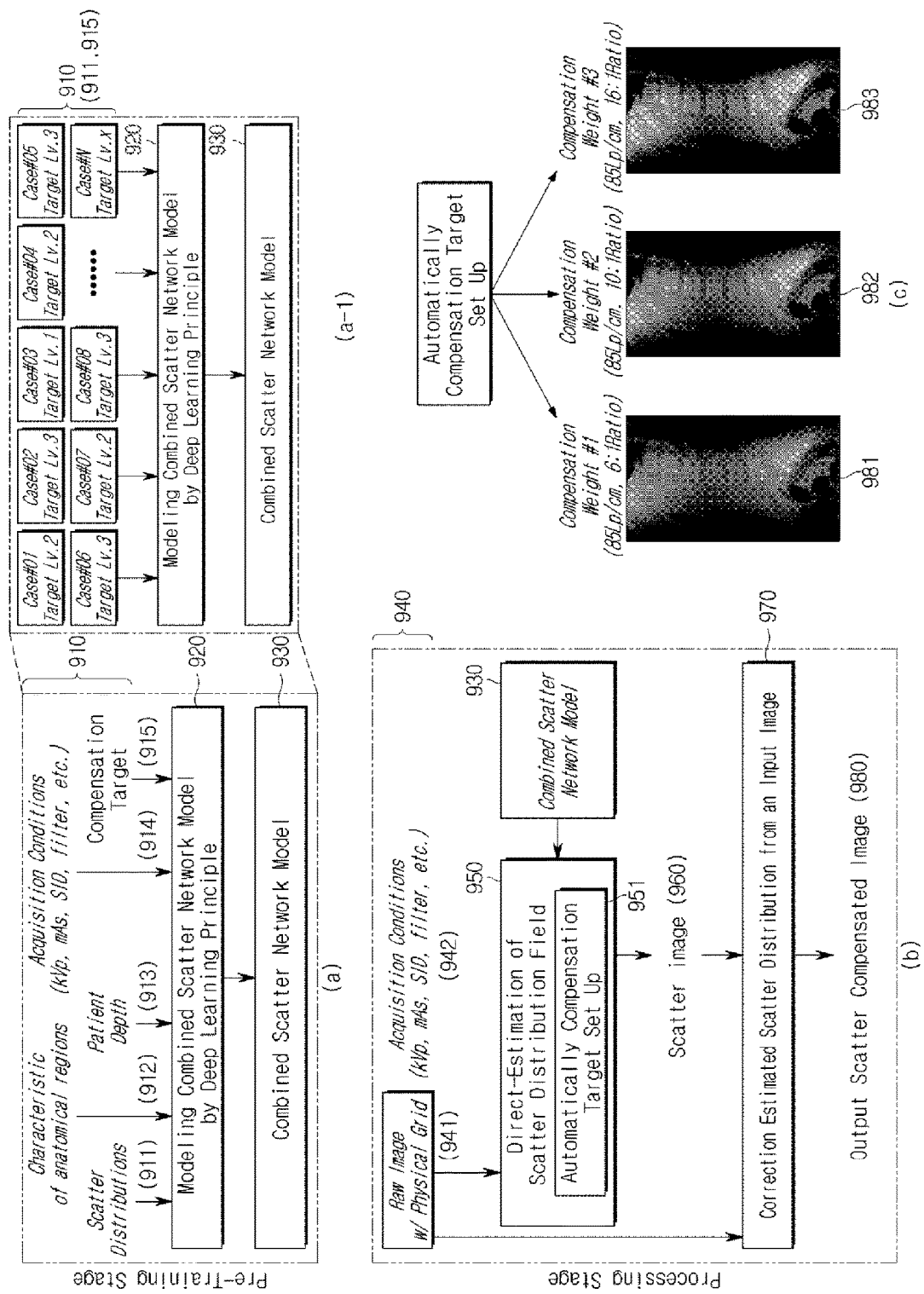
FIGS. 9 and 10 illustrate a process of acquiring a medical image by applying a learning network model to an X-ray apparatus according to an exemplary embodiment of the present disclosure.

FIG. 9 illustrates a process of acquiring a medical image using a learning network model according to an exemplary embodiment of the present disclosure.

Referring to FIG. 9, the X-ray apparatus 100 may automatically provide a medical image having an appropriate intensity of scatter radiation without input of a user unlike what has been described above with reference to FIGS. 7 and 8.

First, in (a) of FIG. 9, a modeling process 920 (e.g., modeling combined scatter network model by deep learning principle) of teaching a learning network model may be performed based on learning data 910 including a scatter radiation image. In this case, the learning data 910 may include, for example, at least one of scatter radiation images 911 (e.g., scatter distributions), characteristics of regions of a target object 912 (e.g., characteristic of anatomical regions), a thickness of the target object 913 (e.g., patient depth), capturing condition information 914 (e.g., acquisition condition (kVp, mAs, SID, filter, etc.)), and a degree of intensity (or compensation) of scatter radiation 915 (e.g., compensation target). In addition, the learning data 910 may include an original radiation image.

In this case, as illustrated in (a-1) of FIG. 9, the scatter radiation images 911 and the degree of intensity of scatter radiation 915 of each scatter radiation image 911 may be provided as a part of the learning data 910. In another exemplary embodiment, when original radiation images are included in the learning data 910, the original radiation images and a degree of intensity of scatter radiation included in each of the original radiation images may be provided as a part of the learning data 910. In another exemplary embodiment, when original radiation images are included in the learning data 910, the original radiation images and a degree of intensity of scatter radiation included in each of scatter radiation-processed medical images acquired from the original radiation images may be provided as a part of the learning data 910.

As a result of performing the modeling process 920, a learning network model 930 (e.g., combined scatter network model) configured to estimate a scatter radiation image may be obtained.

As illustrated in (b) of FIG. 9, when the learning network model 930 is obtained, the X-ray apparatus 100 may perform scatter radiation image estimation 950 (e.g., direct-estimation of scatter distribution field) in which input data 940 is applied to the learning network model 930 configured to estimate scatter radiation. As a result, the X-ray apparatus 100 may acquire a scatter radiation image 960 (e.g., scatter image). In this case, the input data 940 may include, for example, an original radiation image 941 (e.g., raw image with physical grid) and capturing condition information 942 (e.g, acquisition conditions (kVp, mAs, SID, filter, etc.).

Meanwhile, a process 951 (e.g., automatically compensation target set up) of automatically setting a removal degree of scatter radiation may be further included in the scatter radiation image estimation 950. That is, the X-ray apparatus 100 may acquire the scatter radiation image 960 which has an appropriate intensity of scatter radiation, using the learning network model 930, which learned the degree of intensity of scatter radiation corresponding to the original radiation image, in consideration of the degree of intensity of scatter radiation included in the input original radiation image.

Next, the X-ray apparatus 100 may perform scatter processing 970 (e.g., correction estimated scatter distribution from an input image) in which the estimated scatter radiation image 960 is removed from the original radiation image 941.

As a result of the scatter processing 970, the X-ray apparatus 100 may acquire a medical image 980 (e.g., output scatter compensated image) having the appropriate intensity of scatter radiation to satisfy a user.

In FIG. 9, (c) illustrates medical images on which scatter radiation is processed according to the preset removal degree of scatter radiation.

In (c) of FIG. 9, the X-ray apparatus 100 may perform the scatter radiation image estimation 950 and the scatter processing 970 on the original radiation image 941. In this case, the X-ray apparatus 100 may perform the process 951 of automatically setting the removal degree of scatter radiation to automatically acquire a medical image having the appropriate intensity of scatter radiation.

For example, a medical image 981 having the same or similar effect as that of an anti-scatter grid having "85 Lp/cm and 6:1 Ratio" may be acquired when a value of the removal degree is automatically set to be weight #1 (e.g., compensation weight), a medical image 982 having the same or similar effect as that of an anti-scatter grid having "85 Lp/cm and 10:1 Ratio" may be acquired when a value of the removal degree is automatically set to be weight #2, and a medical image 983 having the same or similar effect as that of an anti-scatter grid having "85 Lp/cm and 16:1 Ratio" may be acquired when the value of the removal degree is automatically set to be weight #3.

Figure 10:
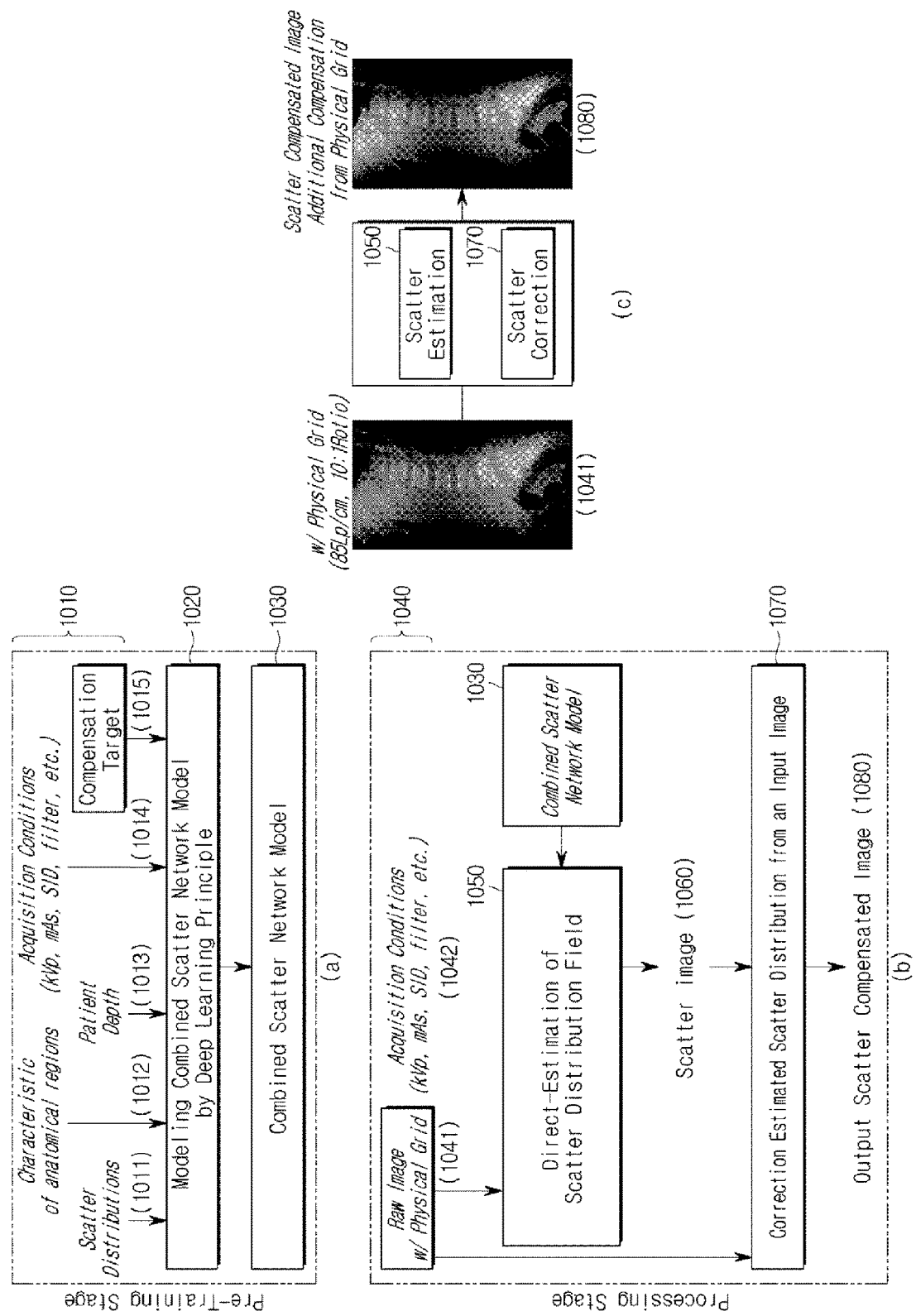

FIG. 10 illustrates a process of acquiring a medical image using a learning network model, according to an exemplary embodiment of the present disclosure.

In FIG. 10, the X-ray apparatus 100 may use a learning network model to further filter scatter remaining after radiation passes through an anti-scatter grid. For example, in the case in which an obese patient is irradiated with X-rays, a considerable amount of scatter radiation may occur in spite of using the anti-scatter grid. In this case, there is a need to remove residual scatter radiation using a learning network model.

First, in (a) of FIG. 10, a modeling process 1020 (e.g., modeling combined scatter network model by deep learning principle) of teaching a learning network model may be performed based on learning data 1010 including a scatter radiation image. In this case, the learning data 1010 may include, for example, at least one of a scatter radiation image 1011 (e.g., scatter distributions), characteristics of regions of a target object 1012 (e.g., characteristic of anatomical regions), a thickness of the target object 1013 (e.g., patient depth), capturing condition information 1014 (e.g., acquisition conditions (kVp, mAs, SID, filter, etc.), and a degree of intensity (compensation or filtering) of scatter radiation 1015 (compensation target). In this case, the scatter radiation image 1011 may be a radiation image captured when an anti-scatter grid is used.

In addition, the learning data 1010 may include an original radiation image. In this case, the original radiation image may be a radiation image captured when an anti-scatter grid is used.

As a result of performing the modeling process 1020, a learning network model 1030 (e.g., combined scatter network model) configured to estimate a scatter radiation image may be obtained.

In (b) of FIG. 10, when the learning network model 1030 is obtained, the X-ray apparatus 100 may perform scatter radiation image estimation 1050 (e.g., direct-estimation of scatter distribution field) in which input data 1040 is applied to the learning network model 1030 configured to estimate scatter radiation. As a result, the X-ray apparatus 100 may acquire a scatter radiation image 1060. In this case, the input data 1040 may include, for example, an original radiation image 1041 (e.g., raw image with physical grid) acquired when an anti-scatter grid is used, and capturing condition information 1042 (e.g., acquisition conditions (kVp, mAs, SID, filter, etc.).

Meanwhile, a process of setting a removal degree of scatter radiation (not shown) may be further included in the scatter radiation image estimation 1050. In this case, the X-ray apparatus 100 may acquire a scatter radiation image having an intensity of scatter radiation corresponding to the removal degree of scatter radiation. The process of setting a removal degree of scatter radiation may be performed through user input via a UI, as illustrated in FIG. 7, or may be automatically set without user input, as illustrated in FIG. 9.

Next, the X-ray apparatus 100 may perform scatter processing 1070 (e.g., correction estimated scatter distribution from an input image) in which the estimated scatter radiation image 1060 is removed from the original radiation image 1041. In this case, the original radiation image 1041 may be a radiation image captured when an anti-scatter grid is used.

As a result of the scatter processing 1070, the X-ray apparatus 100 may acquire a scatter radiation-processed medical image 1080.

In FIG. 10, (c) illustrates radiation images before and after application of the above-described process.

In (c) of FIG. 10, the X-ray apparatus 100 may perform the scatter radiation image estimation 1050 and the scatter processing 1070 on the original radiation image 1041 acquired when an anti-scatter grid is used. In this case, the original radiation image 1041 may be, for example, a radiation image captured when an anti-scatter grid having 85 Lp/cm and 10:1 Ratio is used. As a result of the scatter radiation image estimation 1050 and the scatter processing 1070, the X-ray apparatus 100 may acquire the scatter radiation-processed medical image 1080. In this case, the medical image 1080 may be a clearer medical image than the original radiation image 1040 captured using the anti-scatter grid due to the further performed scatter radiation removal.

Figure 11:
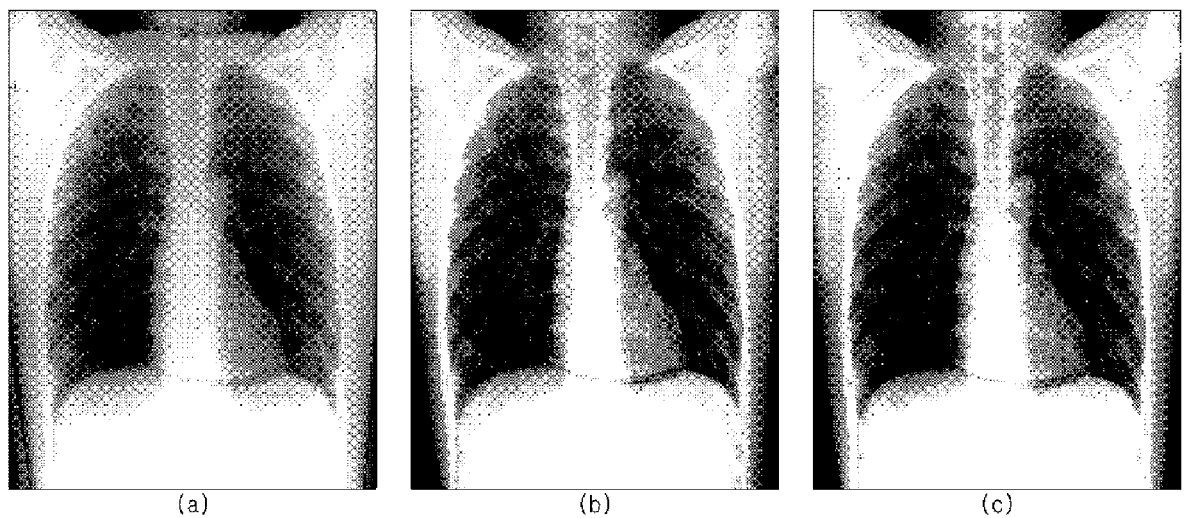
FIG. 11 illustrates images showing scatter radiation treatment effects according to an exemplary embodiment of the present disclosure.

FIG. 11 illustrates images showing a scatter radiation processing effect according to an exemplary embodiment of the present disclosure.

In FIG. 11, (a) illustrates an original radiation image captured when an anti-scatter grid is not used. From the result shown in (a) of FIG. 11, it can be seen that the original radiation image includes a large amount of scatter radiation, and thus has low quality.

In FIG. 11, (b) illustrates an original radiation image captured when an anti-scatter grid is used. Referring to (b) of FIG. 11, it can be seen that an original radiation image having higher quality than that of the original radiation image of (a) of FIG. 11 is acquired due to filtering of scatter radiation through the anti-scatter grid.

In FIG. 11, (c) illustrates a radiation image captured through a scatter radiation image estimation process and a scatter processing process according to an exemplary embodiment of the present disclosure when an anti-scatter grid is not used. Referring to (c) of FIG. 11, the radiation image according to an exemplary embodiment of the present disclosure may have the same or higher quality than that of a radiation image captured using a physical anti-scatter grid.

According to the above-described exemplary embodiments of the present disclosure, a scatter image may be estimated from an original radiation image using a learning network model or a scatter radiation-processed medical image may be directly estimated when an anti-scatter grid is not used.

In addition, to further improve quality of a medical image when an anti-scatter grid is used, a scatter image may be estimated from an original radiation image using a learning network model, or a scatter radiation-processed medical image may be directly estimated.

In addition, when an anti-scatter grid is used or not used, a scatter image may be estimated from an original radiation image using a learning network model considering a removal degree of scatter radiation setting, or a scatter radiation-processed medical image may be directly estimated.

In this case, the process of setting a removal degree of scatter radiation may be performed by a user input via a UI, or the removal degree of scatter radiation may be automatically set without user input.

According to various exemplary embodiments, embodiments of the present disclosure may also be used in stitching techniques for connecting or combining multiple medical images.

For example, the X-ray apparatus 100 may acquire multiple scatter radiation images by inputting multiple original radiation images to a learning network model. In addition, multiple scatter radiation-processed medical images may be acquired based on the acquired multiple scatter radiation images. The X-ray apparatus 100 may acquire an entire medical image of an object by stitching the acquired multiple medical images. In this case, a capturing angle or the like of each of the multiple medical images may be considered together in the process of applying a learning network model or the stitching process.

According to various exemplary embodiments, changes in noise due to scatter radiation may also be used as learning data to teach a learning network model. In this case, a scatter radiation image or a medical image may be estimated in consideration of the noise of scatter radiation.

Figure 12:
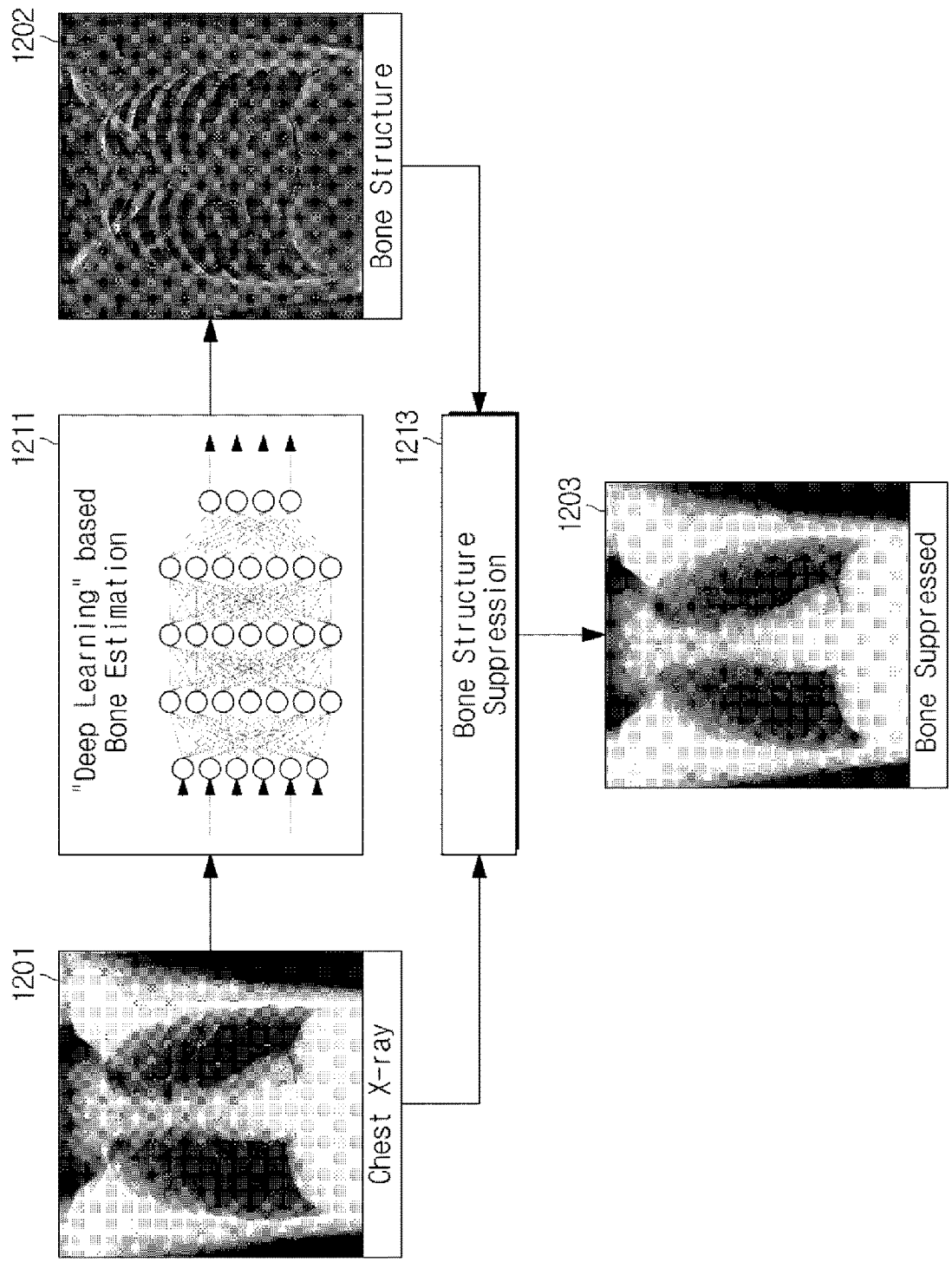
FIGS. 12 to 13B are views illustrating a process of acquiring a medical image, from which a bone structure is removed, by applying a learning network model to an X-ray apparatus according to an exemplary embodiment of the present disclosure.

FIG. 12 illustrates a process of acquiring a medical image from which a bone structure is removed, by applying a learning network model to an X-ray apparatus according to an exemplary embodiment of the present disclosure.

The X-ray apparatus 100 may X-ray photograph a body site (e.g., a human chest) of an object. In this case, visibility of a lesion deteriorates due to bones in the chest, and thus it may be difficult to accurately detect the lesion. Accordingly, it may be necessary to perform a process of estimating a bone in a body site of an object and removing the estimated bone from an original radiation image.

The present disclosure provides a process of removing a bone from an original radiation image using a learning network model.

In FIG. 12, the X-ray apparatus 100 may irradiate a body site (e.g., a chest) with X-rays to acquire an original radiation image 1201. In this case, the original radiation image 1201 may be a medical image acquired using a learning network model configured to estimate scatter radiation, according to the above-described exemplary embodiments.

The X-ray apparatus 100 may perform bone estimation 1211 using a learning network model 1211 (e.g., "deep learning" based bone estimation) configured to estimate a bone from the original radiation image 1201. The learning network model 1211 may include, for example, an AI neural network model or a deep learning network model.

The X-ray apparatus 100 may acquire a bone structure radiation image 1202 as a result of applying the original radiation image 1201 to the learning network model 1211. A bone structure may include, for example, ribs, clavicles, and the like.

When the bone structure radiation image 1202 is acquired, the X-ray apparatus 100 may perform bone processing 1213 (e.g., bone structure suppression) using the original radiation image 1201 and the bone structure radiation image 1202 as an input to acquire a bone structure-processed medical image 1203. In this regard, bone structure processing may include removing at least a portion of the bone structure from the original radiation image 1201, degrading an intensity of at least a portion of the bone structure, filtering at least a portion of the bone structure, or suppressing at least a portion of the bone structure.

As such, by acquiring the medical image 1203 obtained by removing the bone structure from the original radiation image 1201, visibility of a lesion and soft tissue may be improved.

In particular, nodules may not be precisely distinguished in general chest radiation images. In this case, when the bone processing process according to an exemplary embodiment of the present disclosure is performed on the general chest radiation image, lesions hidden by bone may be clearly displayed, and thus accurate lesion detection is enabled.

In addition, an existing bone processing algorithm performs a bone processing process on multiple medical images, while, according to exemplary embodiments of the present disclosure, a sheet of a radiation image is used as input, and thus a radiation dose for an object may be significantly reduced and noise (artifact) of an image due to movement that may mainly occur in cardiology patients may be minimized.

Figure 13A:
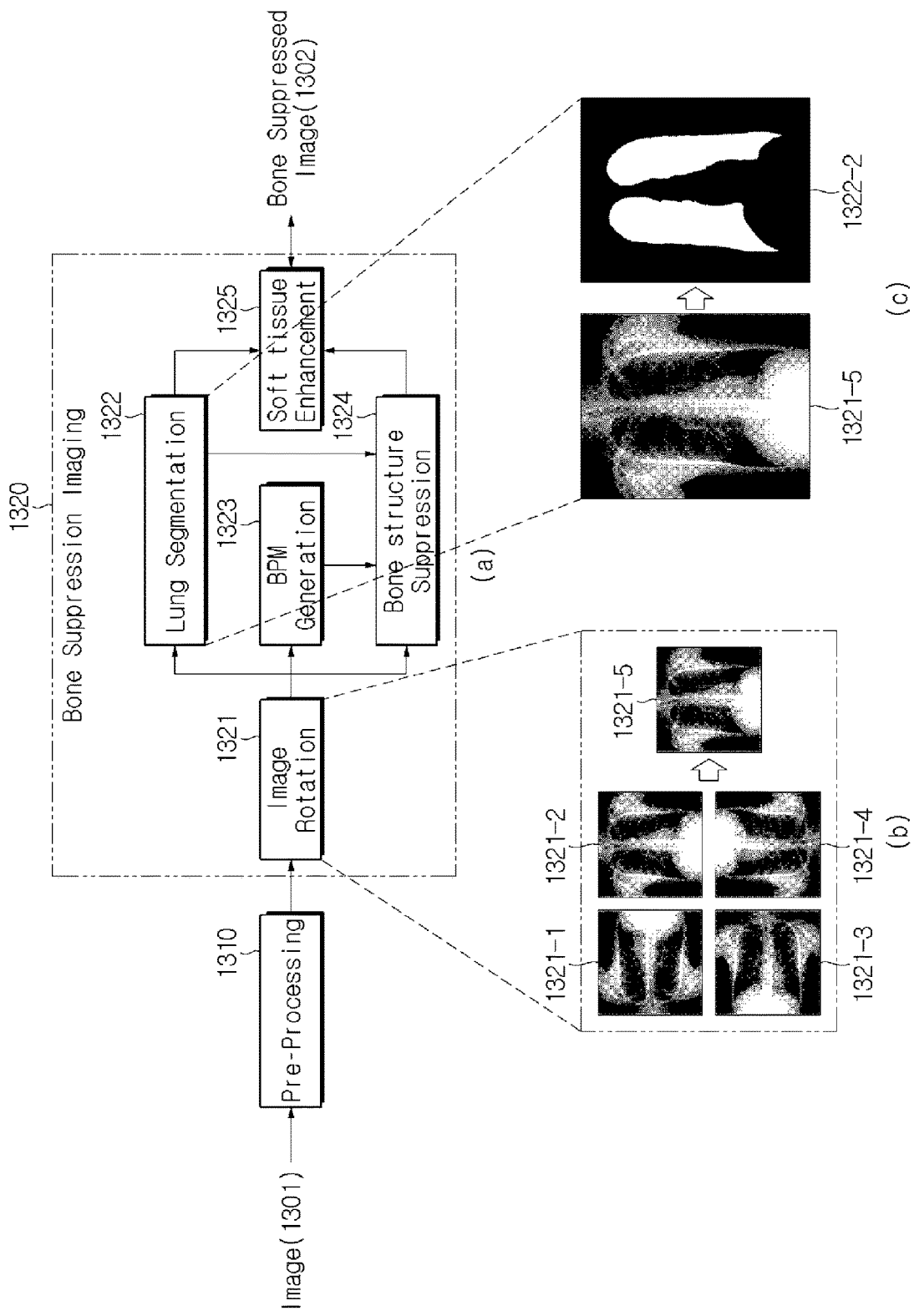
Figure 13B:
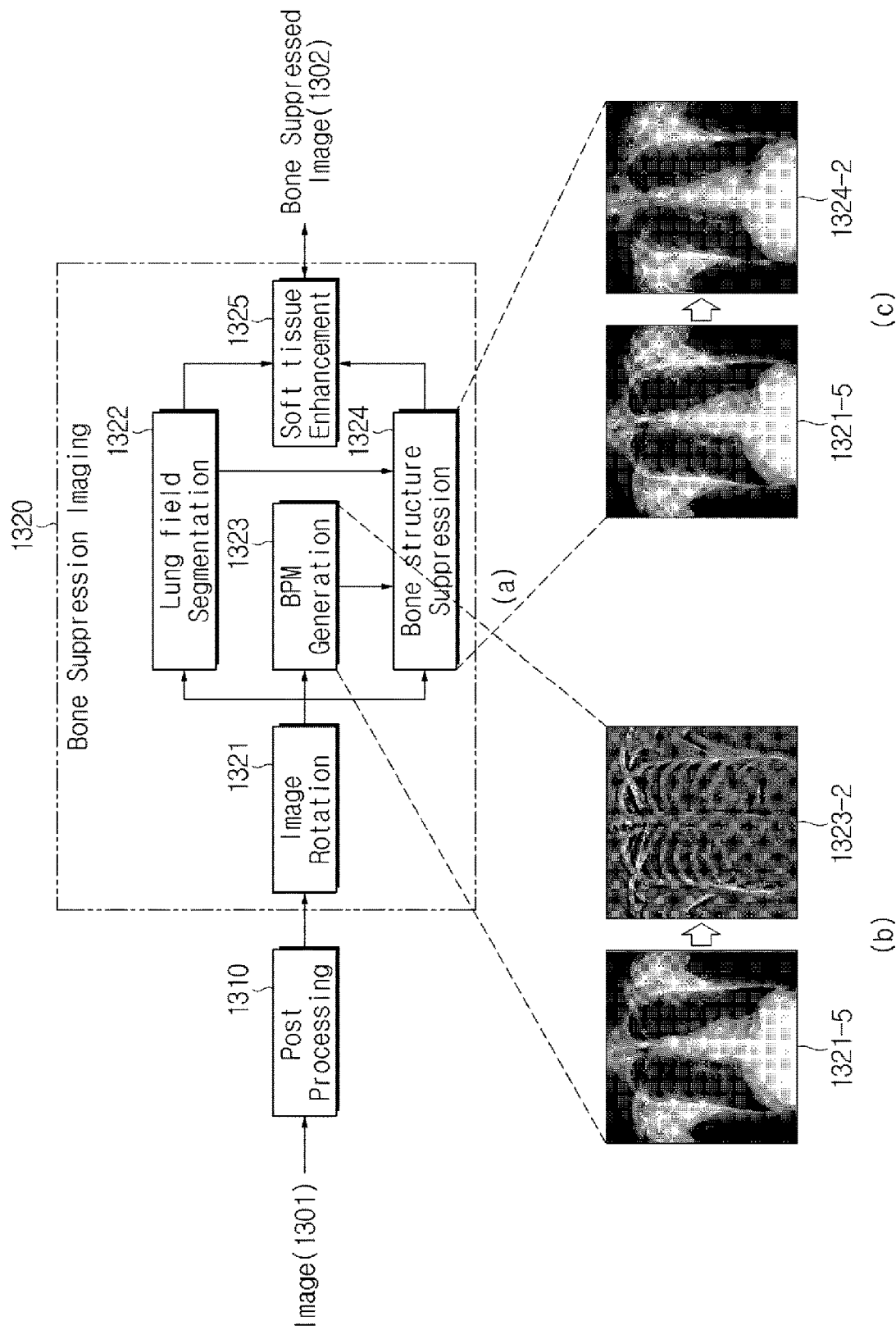

FIGS. 13A and 13B illustrate a process of acquiring a medical image from which a bone structure is removed, by applying a learning network model to an X-ray apparatus according to an exemplary embodiment of the present disclosure.

First, in (a) of FIG. 13A, when a radiation image 1301 of a body site (e.g., a human chest) of an object is acquired, the X-ray apparatus 100 may perform bone processing 1320 (e.g, bone suppression imaging) using the radiation image as an input. In this case, the X-ray apparatus 100 may first perform pre-processing 1310 prior to the bone processing 1320. The pre-processing may include, for example, a method of processing scatter radiation in an original radiation image using the above-described learning network model. In another exemplary embodiment, the pre-processing process may include a process of removing noise of the acquired radiation image, a process of adjusting contrast of the acquired radiation image, or the like.

Next, the X-ray apparatus 100 may perform rotation 1321 in which a radiation image is rotated such that an apex of the chest included in the captured radiation image is directed upward, as a part of the bone processing 1320. For example, referring to (b) of FIG. 13A, radiation images 1321-1 to 1321-4 may be rotated through the pre-processing 1310 such that the apex of a chest is directed upward as in the radiation image 1321-5.

Next, the X-ray apparatus 100 may perform lung segmentation 1322 in which a mask image is produced so that a lung-related region is extracted from the radiation image that underwent the rotation 1321. For example, referring to (c) of FIG. 13A, the X-ray apparatus 100 may produce a mask image 1322-2 from a rotated original radiation image 1321-5 through the lung segmentation 1322. In this case, the process of producing the mask image 1322-2 from the left rotated original radiation image 1321-5 may be performed using a learning network model.

In addition, the X-ray apparatus 100 may perform bone probability map (BPM) generation 1323 in which a bone structure is extracted from the radiation image that underwent the rotation 1321. In this case, the BPM generation 1323 may be performed using a learning network model as described above with reference to FIG. 12.

For example, referring to (b) of FIG. 13B, the X-ray apparatus 100 may produce a bone structure radiation image 1323-2 from the rotated original radiation image 1321-5 through the BPM generation 1323.

Next, the X-ray apparatus 100 may perform a bone processing process 1324 (e.g., bone structure suppression) of acquiring a bone structure-removed radiation image using the rotated original radiation image 1321-5 that underwent the rotation 1321, the bone structure radiation image 1323-2 produced through the BMP generation 1323, and the mask image 1322-2 produced through the lung segmentation 1323. Referring to (c) of FIG. 13B, the X-ray apparatus 100 may produce a bone structure-removed radiation image 1324-2 from the rotated original radiation image 1321-5 through the bone processing 1324.

Next, the X-ray apparatus 100 may perform soft tissue enhancement 1325 in which quality of a soft tissue is enhanced using the mask image 1322-2 produced through the lung segmentation 1322 and the bone structure-removed radiation image 1324-2 produced through the bone processing 1324.

The X-ray apparatus 100 may acquire a final bone structure-removed medical image 1302 having improved soft tissue resolution and contrast, as a result of the soft tissue enhancement 1325.

FIG. 14 is a flowchart illustrating a method of acquiring a medical image using an X-ray apparatus according to an exemplary embodiment of the present disclosure.

First, in operation 1401, the external server 310 or the X-ray apparatus 100 may produce a learning network model configured to estimate scatter radiation by using a plurality of scatter radiation images and a plurality of pieces of capturing condition information related to each of the scatter radiation images. In this case, the external server 310 or the X-ray apparatus 100 may produce the learning network model configured to estimate scatter radiation by also using at least one of characteristics of regions of a target object and a thickness of the target object as learning data.

Next, in operation 1403, when X-ray photographing the object, the X-ray apparatus 100 may acquire an original radiation image of the target object and capturing condition information thereof.

In addition, in operation 1405, the X-ray apparatus 100 may acquire a scatter radiation image related to the original radiation image by inputting the original radiation image and the capturing condition information to the learning network model configured to estimate scatter radiation, according to a calculation based on a connection relationship between a plurality of network nodes of the learning network model and based on a weight of each of the network nodes. In this case, the original radiation image may be an original radiation image of the object captured when an anti-scatter grid is not used. In addition, the capturing condition information may include at least one of a voltage applied to generate X-rays, a current applied to generate the X-rays, a distance from an X-ray emitter to the object, and an energy band of the emitted X-rays, when capturing the original radiation image.

According to various exemplary embodiments, the X-ray apparatus 100 may receive user input to set a removal degree of scatter radiation. In this case, the X-ray apparatus 100 may acquire a scatter radiation image having an intensity of scatter radiation corresponding to the set removal degree of scatter radiation.

According to various exemplary embodiments, when the learning network model configured to estimate scatter radiation is stored in a memory of the external server 310, the X-ray apparatus 100 may transmit the acquired original radiation image and capturing condition information of the object to the external server 310. The external server 310 may acquire a scatter radiation image related to the original radiation image by inputting the received original radiation image and capturing condition information to the stored learning network model. In addition, the external server 310 may transmit the acquired scatter radiation image to the X-ray apparatus 100. The X-ray apparatus 100 may acquire the scatter radiation image transmitted from the external server 310 via a communication unit.

Next, in operation 1407, the X-ray apparatus 100 may acquire a scatter radiation-processed medical image from the original radiation image, based on the original radiation image and the acquired scatter radiation image. In this case, the scatter radiation-processed medical image may be a radiation image obtained by removing scatter radiation from the original radiation image.

Figure 15:
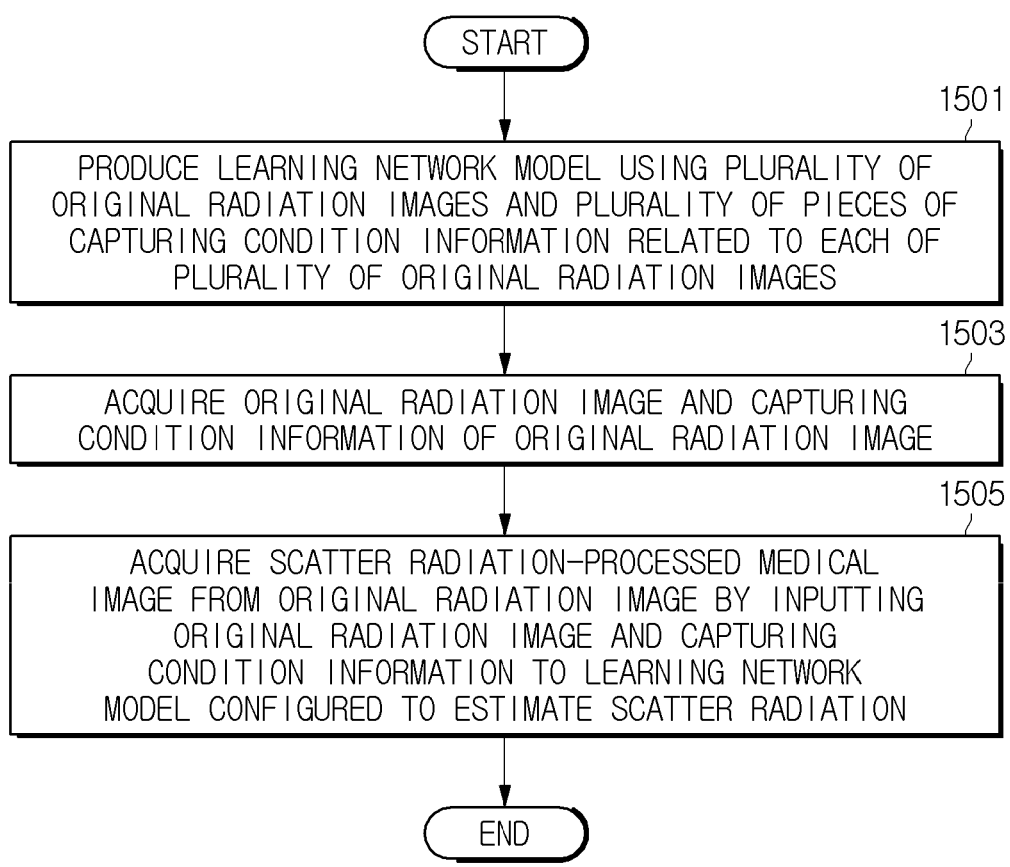

FIG. 15 is a flowchart illustrating a method of acquiring a medical image using an X-ray apparatus according to an exemplary embodiment of the present disclosure.

First, in operation 1501, the external server 310 or the X-ray apparatus 100 may produce a learning network model configured to estimate a scatter radiation-processed medical image by using a plurality of original radiation images and a plurality of pieces of capturing condition information related to each of the original radiation images. In this case, the external server 310 or the X-ray apparatus 100 may produce a learning network model configured to estimate a scatter radiation-processed medical image by also using at least one of characteristics of regions of a target object and a thickness of the target object as learning data.

Next, in operation 1503, when X-ray photographing the object, the X-ray apparatus 100 may acquire an original radiation image of the target object and capturing condition information thereof.

In addition, in operation 1505, the X-ray apparatus 100 may acquire a scatter radiation image related to the original radiation image by inputting the original radiation image and the capturing condition information to the learning network model configured to estimate a scatter radiation-processed medical image, according to a calculation based on a connection relationship between a plurality of network nodes of the learning network model and a weight of each of the network nodes. In this case, the original radiation image may be an original radiation image of the object captured when an anti-scatter grid is not used.

According to various exemplary embodiments, the X-ray apparatus 100 may receive a user input to set a removal degree of scatter radiation. In this case, the X-ray apparatus 100 may acquire a scatter radiation image having an intensity of scatter radiation corresponding to the removal degree of scatter radiation set according to the user input.

According to various exemplary embodiments, when the learning network model configured to estimate a scatter radiation-processed medical image is stored in a memory of the external server 310, the X-ray apparatus 100 may transmit the acquired original radiation image and capturing condition information of the object to the external server 310. The external server 310 may acquire a scatter radiation-processed medical image from the original radiation image by inputting the received original radiation image and capturing condition information to the stored learning network model. In addition, the external server 310 may transmit the acquired medical image to the X-ray apparatus 100. The X-ray apparatus 100 may acquire the medical image transmitted from the external server 310 via a communication unit. In this case, the scatter radiation-processed medical image may be a radiation image acquired by removing scatter radiation from the original radiation image.

The disclosed exemplary embodiments may be implemented as an S/W program including instructions stored in computer-readable storage media.

A computer is a device which calls stored instructions from storage media and is operable in accordance with the disclosed exemplary embodiments according to the called instructions, and may include an X-ray apparatus according to one of the disclosed exemplary embodiments or an external server connected to the X-ray apparatus via communication.

The computer-readable storage media may be provided in the form of non-transitory storage media. The term "non-transitory" as used herein merely means that storage media do not include a signal and are tangible, but does not distinguish between data being stored semi-permanently or temporarily on the storage media.

In addition, methods according to disclosed exemplary embodiments may be provided as a computer program product.

The computer program product may include an S/W program, computer-readable storage media storing the S/W program, or a product transacted between a seller and a buyer.

For example, the computer program product may include a product (e.g., downloadable app) in the form of an S/W program electronically distributed via a manufacturer of an X-ray apparatus or an electronic market (e.g., the Google Play Store or App Store). For electronic distribution, at least a part of the S/W program may be stored in storage media or may be temporarily produced. In this case, the storage media may be a server of a manufacturer or an electronic market, or storage media of an intermediate server.

As is apparent from the above description, when scatter radiation processing is performed on an original radiation image using a learning network model, quality of a medical image acquired by an X-ray apparatus may be improved.

In addition, generally, each of a plurality of scatter kernels considering characteristics of a target object and capturing condition information is needed to perform scatter radiation processing, while, according to embodiments of the present disclosure, integrated estimation of a scatter radiation image is enabled by a learning network model. Accordingly, although a user does not define regularity and does not directly design a network, the network can interpret and perform modelling regularity between images learned on the basis of numerous neurons and combinations thereof.

In addition, in order to continuously improve quality of a medical image, a previously produced learning network model may be continuously trained without a need to generate a novel scatter kernel, resulting in easy management and efficient acquisition of a medical image.

In addition, effects achieved in the present disclosure are not limited to the aforementioned effects, and unmentioned other effects may be clearly understood from the following description by one of ordinary skill in the art to which the present disclosure pertains.

What is claimed is:

1. An X-ray apparatus comprising:
    an X-ray emitter configured to emit X-rays to a target object;
    an X-ray detector configured to detect emitted X-rays that have passed through the object;
    at least one processor configured to control the X-ray emitter and the X-ray detector; and
    a memory connected to the at least one processor,
    wherein the memory is configured to store instructions which, when executed by the at least one processor, cause the at least one processor to:
        acquire an original radiation image of the target object from the X-ray detector;
        acquire a bone structure radiation image of a bone structure included in the target object from the acquired original radiation image using a learning network model, wherein the learning network model is trained to estimate a radiation image corresponding to a bone from a plurality of different radiation images; and
        acquire a medical image in which at least one portion of the bone structure is suppressed from the original radiation image using the bone structure radiation image,
    wherein the learning network model is further trained based on capturing condition information indicating at least one capturing condition corresponding to the plurality of different radiation images.

2. The X-ray apparatus of claim 1, wherein the learning network model includes at least one of an artificial intelligence neural network model or a deep learning network model, and
    wherein the plurality of different radiation images are received from an external device that is external to the X-ray apparatus.

3. The X-ray apparatus of claim 1, wherein the instructions further cause the at least one processor to perform a bone processing process of rotating the original radiation image in a predetermined direction.

4. The X-ray apparatus of claim 3, wherein the instructions further cause the at least one processor use the learning network model to extract the bone structure of the target object from the rotated original radiation image to generate a bone probability map (BPM) from the rotated original radiation image.

5. The X-ray apparatus of claim 4, wherein the instructions further cause the at least one processor to acquire a suppressed radiation image in which the at least one portion of the bone structure is suppressed from the original radiation image, based on the BPM and the original radiation image.

6. The X-ray apparatus of claim 5, wherein the instructions further cause the at least one processor to perform a soft tissue enhancement process of adjusting one or more of a resolution and a contrast of the suppressed radiation image to acquire the medical image.

7. The X-ray apparatus of claim 1, wherein the instructions further cause the at least one processor to generate a mask image in which at least one predetermined region of the target object is extracted from the original radiation image.

8. The X-ray apparatus of claim 1, wherein the instructions further cause the at least one processor to perform preprocessing including at least one from among a scatter process, a noise removal, or a contrast adjustment.

9. A method of controlling an X-ray apparatus, the method comprising:
    emitting X-rays to a target object;
    detecting emitted X-rays that have passed through the object;
    acquiring an original radiation image of the target object from the detected X-rays;
    acquiring a bone structure radiation image of a bone structure included in the target object from the original radiation image using a learning network model, wherein the learning network model is trained to estimate a radiation image corresponding to a bone from a plurality of different radiation images; and
    acquiring a medical image in which at least one portion of the bone structure is suppressed from the original radiation image using the bone structure radiation image,
    wherein the learning network model is further trained based on capturing condition information indicating at least one capturing condition corresponding to the plurality of different radiation images.

10. The method of claim 9, wherein the bone structure radiation image is acquired from the acquired original radiation image using at least one of an artificial intelligence neural network model or a deep learning network model, and
    wherein the plurality of different radiation images are received from an external device that is external to the X-ray apparatus.

11. The method of claim 9, further comprising performing a bone processing process of rotating the original radiation image in a predetermined direction.

12. The method of claim 11, further comprising using the learning network model to extract the bone structure of the target object from the rotated original radiation image to generate a bone probability map (BPM) from the rotated original radiation image.

13. The method of claim 12, further comprising acquiring a suppressed radiation image in which the at least one portion of the bone structure is suppressed from the original radiation image, based on the BPM and the original radiation image.

14. The method of claim 13, further comprising performing a soft tissue enhancement process of adjusting one or more of resolution and a contrast of the suppressed radiation image to acquire the medical image.

15. The method of claim 13, further comprising generating a mask image in which at least one predetermined region of the target object is extracted from the original radiation image.

16. The method of claim 13, further comprising performing preprocessing including at least one from among a scatter process, a noise removal, or a contrast adjustment.

* * * * *